(12) United States Patent
Warren et al.

(10) Patent No.: US 12,198,787 B2
(45) Date of Patent: Jan. 14, 2025

(54) ESTIMATING PROPERTIES OF SURFACTANT MIXTURES

(71) Applicant: United Kingdom Research and Innovation, Swindon Wiltshire (GB)

(72) Inventors: Patrick Warren, Cheshire (GB); David Bray, Cheshire (GB); Richard Anderson, Cheshire (GB); Annalaura Del Regno, Mannheim (DE)

(73) Assignee: United Kingdom Research and Innovation, Swindon Wiltshire (GB)

( * ) Notice: Subject to any disclaimer, the term of this patent is extended or adjusted under 35 U.S.C. 154(b) by 444 days.

(21) Appl. No.: 17/665,040

(22) Filed: Feb. 4, 2022

(65) Prior Publication Data

US 2022/0254454 A1 Aug. 11, 2022

(30) Foreign Application Priority Data

Feb. 9, 2021 (GB) ...................................... 2101749

(51) Int. Cl.
*G16C 10/00* (2019.01)
(52) U.S. Cl.
CPC .................................. *G16C 10/00* (2019.02)
(58) Field of Classification Search
None
See application file for complete search history.

(56) References Cited

U.S. PATENT DOCUMENTS

| | | | |
|---|---|---|---|
| 2012/0101862 A1* | 4/2012 | Stanton | G06Q 10/00 705/7.11 |
| 2020/0168301 A1* | 5/2020 | Pyzer-Knapp | G16C 20/30 |
| 2021/0020273 A1* | 1/2021 | Klamt | G16C 20/30 |

FOREIGN PATENT DOCUMENTS

CN 112652364 A 4/2021

OTHER PUBLICATIONS

The Marcules and Related Equations, exceprt from Phase Equilibria in Chemical Engineering, Walas, 1985.
(Continued)

*Primary Examiner* — Lisa M Caputo
*Assistant Examiner* — Cynthia L Davis
(74) *Attorney, Agent, or Firm* — Lempia Summerfield Katz LLC

(57) ABSTRACT

Methods and apparatus for estimating properties of a mixture of two or more surfactant species are provided. Multiple molecular dynamics simulations of the mixture are performed, each simulation using a particular total concentration of the surfactant species and a particular ratio of the surfactant species, such that the multiple simulations cover a plurality of such total concentrations and a plurality of such ratios, each simulation being carried out above the critical micelle concentration of the simulated mixture. For each simulation, and from the results of each simulation, a distribution of each surfactant species between at least a micellar pseudo-phase and a non-micellar pseudo-phase of the mixture at the particular total concentration and particular ratio for that simulation is determined. A thermodynamic model of the mixture is then fitted to the distributions to determine fitted parameters of the thermodynamic model, and the one or more properties are estimated using the thermodynamic model and the fitted parameters.

20 Claims, 9 Drawing Sheets

(56) References Cited

OTHER PUBLICATIONS

Anderson RL, et al. (2017) Dissipative particle dynamics: systematic parametrization using water-octanol partition coefficients. J. Chem. Phys. 147:094503.
Anderson RL, et al. (2018) Micelle formation in alkyl sulfate surfactants using dissipative particle dynamics. J. Chem. Theory Comput. 14:2633-2643.
Anogiannakis SD, Petris PC, Theodorou DN (2020) Promising route for the development of a computational framework for self-assembly and phase behavior prediction of ionic surfactants using Martini. J. Phys. Chem. B 124:556-567.
Bales BL (2001) A definition of the degree of ionization of a micelle based on its aggregation No. J. Phys. Chem. B 105:6798-6804.
Bray DJ, Regno AD, Anderson RL (2020) UMMAP: a statistical analysis software package for molecular modelling. Mol. Simul. 46:308-322.
Chen H, Panagiotopoulos AZ (2019) Molecular modeling of surfactant micellization using solvent-accessible surface area. Langmuir 35:2443-2450.
Danov KD, Kralchevsky PA, Ananthapadmanabhan KP (2014) Micelle-monomer equilibria in solutions of ionic surfactants and in ionic-nonionic mixtures: A generalized phase separation model. Adv. Colloid Interf. Sci. 206:17-45.
Del Regno A. et al., "Critical Micelle Concentrations in Surfactant Mixtures and Blends by Simulation" Journal of Physical Chemistry B, vol. 125 Issue 22, May 27, 2021 pp. 5983-5990.
Eslami H, Khani M, Muller-Plathe F (2019) Gaussian charge distributions for incorporation of electrostatic interactions In dissipative particle dynamics: application to self-assembly of surfactants. J. Chem. Theory Comput. 15:4197-4207.
Español P, Warren PB (2017) Perspective: dissipative particle dynamics. J. Chem. Phys. 146:150901.
Holland PM (1986) Nonideal mixed micellar solutions. Adv. Colloid Interf. Sci. 26:111-129.
Holland PM, Rubingh DN (1983) Nonideal multicomponent mixed micelle model. J. Phys. Chem. 87:1984-1990.
Jiao S, Santos AP, Panagiotopoulos AZ (2018) Differences in free surfactant concentration and aggregation properties for amphiphiles with the same critical micelle concentration. Fluid Phase Equilibr. 470:126-133.
Kamrath RF, Franses EI (1983) Thermodynamics of mixed micellization. pseudo-phase separation models. Ind. Eng. Chem. Fundam. 22:230-239.
Kamrath RF, Franses EI (1984) Mass-action model of mixed micellization. J. Phys. Chem. 88:1642-1648.
Kamrath RF, Franses EI (1984) Thermodynamics of partially miscible micelles and liquid crystals in Surfactants in Solution, ed. Mittal, K. L. and LB. (Springer, Boston, MA), pp. 129-142.
Kamrath RF, Franses EI (1986) New mathematical models of mixed micellization in Phenomena in Mixed Surfactant Systems, ACS Symposium Series vol. 311, ed. Scamehorn JF. pp. 44-60.
Lavagnini E, Cook JL, Warren PB, Williamson MJ, Hunter CA (2020) A surface site interaction point method for dissipative particle dynamics parametrization: application to alkyl ethoxylate surfactant self-assembly. J. Phys. Chem. B 124:5047-5055.
McDonagh JL, Shkurti A, Bray DJ, Anderson RL, Pyzer-Knapp EO (2019) Utilizing machine learning for efficient parameterization of coarse grained molecular force fields. J. Chem. Theory Comput. 59:4278-4288.
Panoukidou M, Wand CR, Del Regno A, Anderson RL, Carbone P (2019) Constructing the phase diagram of sodium aurylethoxysulfate using dissipative particle dynamics. J. Colloid Interf. Sci. 557:34-44.
Penfold J, et al. (1995) Solution and adsorption behavior of the mixed surfactant system sodium dodecyl sulfate/n-hexaethylene glycol monododecyl ether. Langmuir 11:2496-2503.
Seaton MA, Anderson RL, Metz S, Smith W (2013) DLMESO: highly scalable mesoscale simulations. Mol. Simul. 39:796-821.
Shinoda K (1954) The critical micelle concentration of soap mixtures (two-component mixture). J. Phys. Chem. 58:541-544.
Shinoda K, Hutchinson E (1962) Pseudo-phase separation model for thermodynamic calculations on micellar solutions. J. Phys. Chem. 66:577-582.
Smith GN, Brown P, Rogers SE, Eastoe J (2013) Evidence for a critical micelle concentration of surfactants in hydrocarbon solvents. Langmuir 29:3252-3258.
Taddese T, Anderson RL, Bray DJ, Warren PB (2020) Recent advances in particle-based simulation of surfactants. Curr. Opin. Colloid Interf. Sci. 48:137-148.
Tokiwa F (1968) Solubilization behavior of sodium dodecyl polyoxyethylene sulfates in relation to their polyoxyethylene chain lengths. J. Phys. Chem. 72:1214-1217.
UK Search Report from GB2101749.6, dated Jul. 12, 2021, 1 page.
Van der Walt S, Colbert SC, Varoquaux G (2011) The NumPy array: A structure for efficient numerical computation. Comput. Sci. Eng. 13:22-30.
Virtanen P, et al. (2020) SciPy 1.0: Fundamental Algorithms for Scientific Computing in Python. Nat. Methods 17:261-272.

\* cited by examiner

ESTIMATING PROPERTIES OF SURFACTANT MIXTURES

RELATED APPLICATIONS

This application claims the benefit of GB 2101749.6, filed on Feb. 9, 2021, which is hereby incorporated by reference in its entirety.

BACKGROUND

Surfactants are widely used in areas ranging from home and personal care settings, through manufacturing processes, to biomedical applications such a drug delivery systems. A major driver for innovation is the need to support decarbonisation of the market, moving away from petrochemical and traditional plant-based feedstocks towards sustainably-sourced raw materials.

Surfactants readily self-assemble in aqueous solution into supramolecular aggregates known as micelles, which typically comprise 20-100 surfactant molecules. The concentration where micelles first appear is known as the critical micelle concentration (CMC). In applications, the CMC has become a key design target because it is correlated with a multitude of practically relevant physico-chemical properties, such as a minimum in interfacial tension and a maximum in detergency. As surfactants are widely used in applications ranging from manufacturing processes through to home and personal care products, a significant effort has been expended to develop thermodynamic models which can be used to predict and optimize the CMC.

Rapid decarbonisation of the current multi-billion dollar surfactant market (moving away from petrochemicals and traditional plant-based feedstocks towards sustainably-sourced raw materials) is driving an urgent need to update these models. In this field therefore, computer-aided formulation and design practices can play a significant role in screening new surfactants, accelerating deployment to market, de-risking scale-up, improving the ability to deal with raw materials variability, and sharpening raw materials specifications.

Almost all applications involve surfactant mixtures, not only because blending is a key enabler for quality control and simultaneous optimisation of multiple end-point properties, but also because raw materials tend to be inherently polydisperse and may contain impurities. To give a concrete example of the latter, widely used in personal care products such as shampoos and other isotropic liquids, sodium laureth sulfates (SLESs) are anionic surfactants with an ethoxylate (EO) spacer group inserted between the hydrocarbon tail and the negatively-charged sulfate headgroup. The CMC of pure SLES2 (chemical formula $CH_3(CH_2)_{11}(OCH_2CH_2)_2 OSO_3Na$; MW=376) is 3.1 mM or 1.17 g/l. However the CMC of a commercial SLES with 2 moles of EO such as STEOL CS-270 is reported by the manufacturer to be only 0.28 g/l. This four-fold difference might be attributed to polydispersity in the ethoxylate spacer length, small amounts of unsulfated alkyl ethoxylates, trace amounts of salt, or a combination of all of these, in the commercial material.

It would be desirable to address problems and limitations of the related prior art.

SUMMARY

This disclosure addresses the challenging problem of predicting the behaviour of surfactant mixtures. Traditional experimental methods of characterising surfactant mixtures typically involve determining the CMC as a function of composition by tracking the behaviour of a physico-chemical property such as surface tension as a function of concentration.

In contrast, an approach taken in the present disclosure is to use coarse-grained molecular dynamics simulations to predict critical micelle concentrations (CMCs) in binary and polydisperse surfactant mixtures and blends. By fitting thermodynamic models, and in particular pseudo-phase separation models (PSMs) to mixtures at selected compositions above the CMC, computationally expensive simulations of multicomponent mixtures as a function of dilution are avoided. The fitted PSMs can then be used to compute the CMC as a function of composition. With suitably generalised meta-models, this can also be extended to make predictions of the CMC in polydisperse blends. The approach is demonstrated for example for sodium laureth sulfate (SLES) surfactants with polydispersity in the ethoxylate spacer.

Formally derivable from mass-action models in the limit of large aggregation numbers (17), the PSMs used exploit an analogy to vapor-liquid equilibrium (VLE) wherein surfactants in micelles are treated as being in a (liquid-like) micellar pseudo-phase, in coexistence with a (vapor-like) dilute solution of monomers; thus apart from very refined models it is only in the micellar pseudo-phase that one has to worry about non-ideality. Here, the use of regular solution theory, or more formally Margules or Redlich-Kister type activity models (18), introduces empirical non-ideal mixing parameters which become the target of the above fitting procedure. In this respect, rather than fitting the PSM to an experimentally determined CMC as a function of composition, and using that to predict the solution state at higher concentrations, we do the reverse.

In particular, the invention provides a method of estimating one or more properties of a mixture of two or more surfactant species, comprising: performing a plurality of molecular dynamics simulations of the mixture, each simulation using a particular total concentration of the surfactant species and a particular ratio of the surfactant species, such that the plurality of simulations cover a plurality of such total concentrations and a plurality of such ratios, each simulation being carried out above the critical micelle concentration of the simulated mixture; determining, for each simulation, and from the results of each simulation, a distribution of each surfactant species between at least a micellar pseudo-phase and a non-micellar pseudo-phase of the mixture at the particular total concentration and particular ratio for that simulation; fitting a thermodynamic model of the mixture to the distributions to determine fitted parameters of the thermodynamic model; and estimating the one or more properties using the thermodynamic model and the fitted parameters.

In particular, the mixture of two or more surfactant species may be a mixture in aqueous solution, and the ratio of the surfactant species may be a ratio of the mole fractions of each of those species within the surfactants present. The invention may be implemented using a binary mixture of two surfactant species, or using more than two species in the mixture.

The one or more properties which are estimated may for example comprise the critical micelle concentration of the mixture at one or more ratios of the surfactant species, and/or a ratio of the two or more surfactant species estimated to provide the mixture with a target critical micelle concentration. The fitted thermodynamic model may also be used to estimate one or more properties of a mixture of surfactants comprising one or more further surfactant species in addition to the two or more surfactant species.

The thermodynamic model may in particular be, or comprise, a pseudo-phase separation model (PSM). Such a PSM may express the balance between a micellar and a non-micellar pseudo-phase in terms of energy such as Gibbs free energy. More generally, the thermodynamic model may be or comprise a mass action model. The fitted parameters may comprise a plurality of non-ideal mixing parameters representing mixing of the two or more surfactant species, according to the mixing model, in the micellar pseudo-phase. These non-ideal mixing parameters may be used in the thermodynamic model to determine an activity coefficient for each surfactant species within the micellar pseudo-phase.

Typically, the non-ideal mixing parameters may be constants, for the mixture of surfactant species, of a Margules model or other non-ideal mixing model comprised in the thermodynamic model. The fitted parameters may be determined so as to minimise differences between concentrations of the surfactant species in the non-micellar pseudo-phase as calculated by the thermodynamic model and those concentrations according to the distributions resulting from the simulations.

In more detail, the thermodynamic model or pseudo-phase separation model may comprise a plurality of relationships each relating a critical micelle concentration for a particular surfactant species with the distribution of that species between the micellar and non-micellar pseudo-phases, such relationships optionally also including the activity coefficient for that species within the micellar pseudo-phase. The thermodynamic model may also comprise or be supplemented by a mass balance relationship for the surfactant species in the two phases, and may also comprise the above mixing model such as a Margules model relating the activity coefficients to a set of mixing parameters.

Data processing aspects of the described method, such as those set out above, may be described as a computer implemented method, and may be carried out on one or more suitable computer systems. Such methods may for example be carried out automatically and without user or human intervention. The invention also provides a computer program product comprising computer program code arranged to carry out the above methods when executed on one or more suitable computer systems, and one or more computer readable media carrying such computer program code.

Such computer systems may comprise one or more processors for carrying out the described data processing operations under the control of suitable computer software or program elements, in combination with suitable memory for storing such program elements and data required for the data processing steps, suitable data interfaces such as network connections, input devices such as keyboard and mouse, and output devices such as a visual display unit. Such computer systems may be located at a single site or at multiple sites.

Having carried out the described methods to estimate properties of a surfactant mixture, the invention may further provide making or manufacturing the mixture of two or more surfactant species so as to have one or more of the estimated properties. For example, the mixture may be made or manufactured to have a ratio of the two or more surfactant species which is estimated using the thermodynamic model and fitted parameters to have a predefined target critical micelle concentration.

The made or manufactured mixture may for example be or be comprised within one of: a cosmetic product, a food or drink product, a cleaning product, a lubricant, a medicament, and a paint.

The invention also provides apparatus arranged to carry out the above methods, for example apparatus for modelling a mixture of two or more surfactant species, comprising: a molecular dynamics simulator arranged to perform a plurality of molecular dynamics simulations of the mixture, each simulation using a particular total concentration of the surfactant species and a particular ratio of the surfactant species, such that the plurality of simulations cover a plurality of such total concentrations and a plurality of such ratios, each simulation being carried out above the critical micelle concentration of the simulated mixture; a distribution analyser arranged to determine, for each simulation, and from the results of each simulation, a distribution of each surfactant species between at least a micellar pseudo-phase and a non-micellar pseudo-phase of the mixture at the particular total concentration and particular ratio for that simulation; and a parameter fitting unit arranged to fit a thermodynamic model of the mixture to the distributions to determine fitted parameters of the thermodynamic model.

The apparatus may further comprise a property estimator unit arranged to estimate one or more properties of the mixture of the two or more surfactant species using the thermodynamic model and the fitted parameters, for example to estimate the critical micelle concentration of the mixture at one or more ratios of the surfactant species; a ratio of the two or more surfactant species estimated to provide the mixture with a target critical micelle concentration; and one or more properties of a mixture of surfactants comprising the two or more surfactant species, and one or more further surfactant species.

The molecular dynamics simulator, the distribution analyser, parameter fitting unit, and any other such functional elements of the apparatus may be implemented in software on one or more computer systems as discussed above, typically including one or more computer processors, suitable program and data storage, and suitable input and output facilities including for example a data network connection, keyboard, mouse, display screen and so forth. The described apparatus may be arranged to carry out the described modelling of a mixture of surfactant species automatically and without human intervention, subject for example to a human operator arranging for the appropriate parameters and data for the modelling to be in place.

BRIEF DESCRIPTION OF THE DRAWINGS

Embodiments of the invention will now be described, by way of example only, with reference to the accompanying drawings of which:

FIG. 3b illustrates how surfactant mixtures and products containing such mixtures may be made or manufactured with critical micelle concentration and/or other properties estimated using the apparatus of FIG. 1 or 2 or the method of FIG. 3a;

DETAILED DESCRIPTION

The present disclosure relates to methods and apparatus for estimating one or more properties of a mixture of two or more surfactant species, typically in an aqueous solution. Such properties may include, for example, a critical micelle concentration for a particular mole fraction ratio or other ratio of the species in the mixture.

Figure 1:
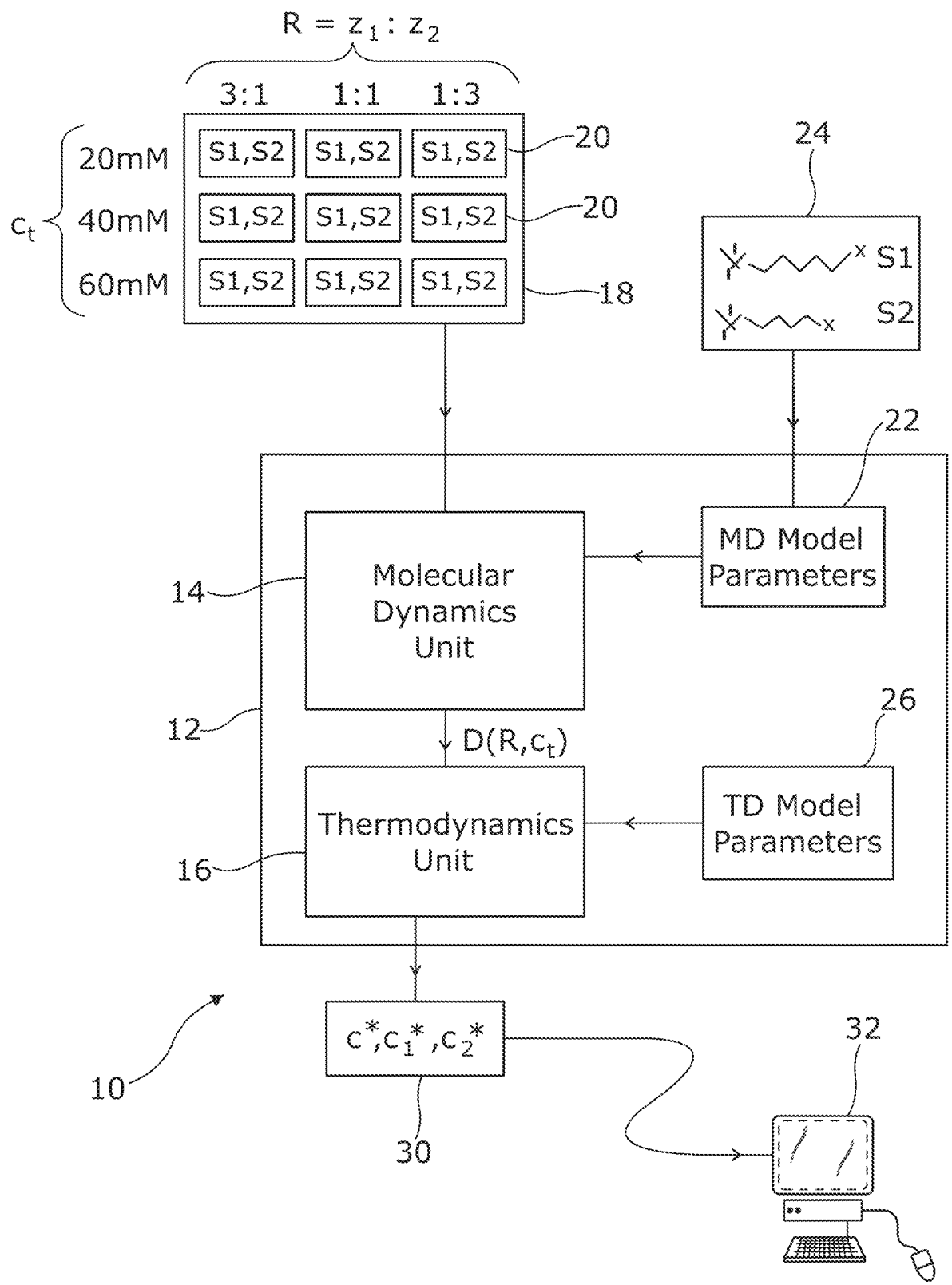
FIG. 1 illustrates computer apparatus arranged to estimate critical micelle concentration of a mixture of surfactants in a solution. The mixture may be a binary mixture of two surfactant species, or a polydisperse blend.

Referring to FIG. 1 there is illustrated computer apparatus 10 arranged to estimate one or more properties of a mixture of two or more surfactant species S1, S2 such as the critical micelle concentration c* of the mixture, at each of one or more concentration or mole fraction ratios (denoted as $R=z_1:z_2$ in the figure) of the constituent surfactant species.

The apparatus comprises a surfactant properties estimator 12 which itself comprises a molecular dynamics unit 14 and a thermodynamics unit 16. The molecular dynamics unit 14 is arranged to carry out molecular dynamics simulations of multiple different formulations of the mixture, for example at multiple ratios R of concentrations or mole fractions of the constituent surfactant species S1, S2, and at multiple total concentrations $c_t$ of all of the surfactant species together, each simulation typically being for just one such formulation. Each such simulated formulation is above the critical micelle concentration c*, so that in each simulation micelles are sustained in the simulated mixture.

The molecular dynamics unit 14 then also analyses the simulated surfactant mixture at one or more time points of each simulation to determine distributions of the surfactant species within the simulations, for example distribution or partition of each of the surfactant species between the simulated micelles on the one hand (which will typically each comprise surfactant molecules of all of the species), and outside of the simulated micelles on the other (which will typically include surfactant monomers and clusters which are deemed sub-micellar according to some criterion such as a maximum cluster size, say up to around 5 to 10 molecules). If surfactant molecules within micelles are said to constitute a micellar pseudo-phase, and other surfactant molecules in the simulation a non-micellar pseudo-phase, then such a distribution may define the distribution or partition of each surfactant species between at least a micellar pseudo-phase and a non-micellar pseudo-phase of the mixture, at the particular formulation such as total concentration and particular constituent species mole fraction ratio for that simulation. This distribution data D is then passed to the thermodynamics unit 16 for subsequent use as described below. If the formulations vary in terms of species ratio R and total concentration $c_t$, then D may be a data set $D(R,c_t)$ as shown in FIG. 1.

FIG. 1 also shows a simulation matrix 18 which acts as a control matrix for the molecular dynamics unit 14. Each of multiple simulation parameter sets 20 of the control matrix 18 defines a particular formulation of the surfactant mixture to be simulated. In the illustrated example nine different formulations are illustrated, covering all nine different combination of three different species ratios (3:1, 1:1 and 1:3), and three different total surfactant concentrations (20 mM, 40 mM and 60 mM) of a mixture of the species S1, S2. The duplication of each simulation parameter set 20 in the figure illustrates that for each formulation the dynamics simulation may be run two, or more times. In this way, distribution data D for each formulation may be an average over either or both of (i) multiple time points within each simulation of that formulation, and (ii) multiple such simulations of that formulation.

The molecular dynamics simulations carried out by the molecular dynamics unit 14 may be controlled by a set of molecular dynamics (MD) model parameters 22. Such parameters may define for example the way in which interactions between the surfactant species S1, S2, and interactions of these species with other entities such as water molecules, are included within the simulation, and other factors. To this end, the MD model parameters 22 may be partly set to reflect surfactant definitions 24 for the surfactant species S1, S2 to be simulated. Although in FIG. 1 only two surfactant species S1, S2 are shown, the apparatus may be operated to estimate properties of a mixture of more than two surfactant species, including mixtures of three, four, or more such species.

The molecular dynamics simulations typically track or simulate the physical movements of each of a large number (for example around 1000) of the modelled surfactant molecules, over a large number of suitable time steps (for example around $1\times10^7$ time steps), these movements being subject to the interactions between the molecules as defined by the MD model parameters 22, within a physical model space of appropriate size to achieve the desired surfactant concentrations. More detailed description of how the molecular dynamics simulations may be carried out is provided below. Such techniques are described in detail for example in Español P and Warren P B (2017) "Perspective: dissipative particle dynamics", *J. Chem. Phys.* 146:150901, which is hereby incorporated by reference for these and all other purposes.

The thermodynamics element 16 receives the distribution data D from the molecular dynamics simulations carried out above the critical micelle concentrations of the simulated surfactant mixture formulations, and uses a thermodynamics based model to estimate one or more bulk properties of the mixture, such as critical micelle concentrations at one or more ratios of the component surfactant species, or ratio of the species to provide a target critical micelle concentration.

In contrast to the molecular dynamics simulations, the thermodynamics based model is typically an analytical model comprising a limited set of equations defining the mixture as a whole, even if it is typically necessary to handle the thermodynamics model using numerical techniques in order to fit to, or make estimations from, this model. In particular, the thermodynamics based model may relate the Gibbs free energy, of each surfactant species within the micelles (within the micellar pseudo-phase) and outside of the micelles (within the non-micellar pseudo-phase), for example using a pseudo-phase separation model, typically in conjunction with other relationships such as a surfactant species mass balance and a mixing model for the surfactant species within the micellar pseudo-phase.

The use of pseudo-phase separation models for estimating bulk properties such as critical micelle concentration is described for example in Kamrath R F and Franses E I (1986) "New mathematical models of mixed micellization", Phenomena in Mixed Surfactant Systems, ACS Symposium Series vol 311, ed. Scamehorn J F, pp 44-60, hereby incorporated by reference for this and all other purposes.

The thermodynamics unit 16 may operate using one or more thermodynamic (TD) model parameters 26, including for example species specific ion binding parameters. Typically, the thermodynamics unit 16 may then be arranged to fit certain parameters of the thermodynamics based model, such as mixing parameters or non-ideal mixing parameters of the surfactant species within the micellar pseudo-phase, to the distributions D received from the molecular dynamics unit. In particular, such a fit may seek values for these parameters such that differences between the some or all of the data of distributions D, and the corresponding values predicted by the thermodynamic model, are minimized, for example according to a least squares or similar function. Having fitted such parameters the thermodynamics model can then be used to estimate bulk parameters of the surfactant mixture such as critical micelle concentration.

As illustrated in FIG. 1, one or more estimated properties 30 of the surfactant mixture as calculated by the thermodynamics unit 16 using the fitted parameters may then be output by the surfactant properties estimator 12. As noted above, these properties may include the critical micelle concentration c* at one or more different ratios of the surfactant species, and the critical micelle concentration $c_1^*$, $c_2^*$ of particular surfactant species, but also other properties may be calculated and output such as one or more ratios of the component surfactant species which are expected to give rise to a particular critical micelle concentration, and various properties of the surfactant mixture above the critical micelle concentration. These estimated properties may be displayed, stored, transmitted, and/or used in various ways. For example, in FIG. 1 the output properties are shown as transmitted over a network to a personal computer 32 for display and further use.

The surfactant properties estimator 12 of FIG. 1 may itself be implemented on a single computer system, or distributed across multiple computer systems, typically being implemented using computer program code on such computer systems. Each such computer system will typically comprise one or more microprocessors coupled to suitable computer memory for carrying both program code and data relating to the operation of the surfactant properties estimator, suitable in/out facilities, network connections to other computer systems, non-volatile memory such as Flash or hard disk storage and so forth.

The execution of the molecular dynamics simulations by the molecular dynamics unit may typically require very large amounts of computational resource, and may therefore be implemented on massively parallel or other high performance computer systems. In order to reduce the elapsed time required to execute all of the required molecular dynamics simulations, these could for example be executed in parallel on a massively parallel high performance system.

Figure 2:
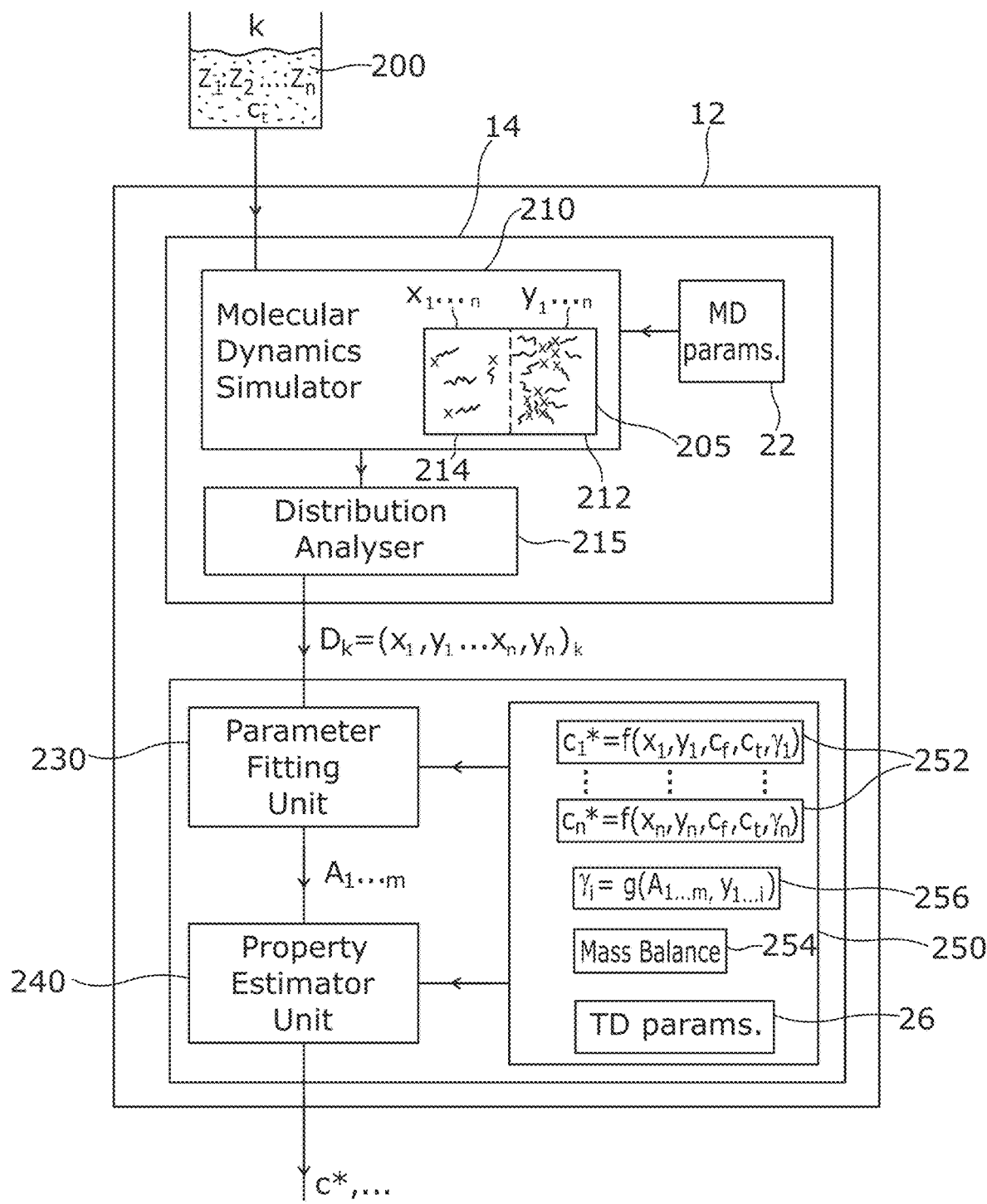
FIG. 2 shows molecular dynamics modelling and thermodynamics model aspects of FIG. 1 in more detail.

FIG. 2 illustrates in more detail how the surfactant properties estimator 12 of FIG. 1 may be implemented. In FIG. 2, the molecular dynamics unit 14 comprises a molecular dynamics simulator 210 and a distribution analyser 215. The molecular dynamics simulator 210 executes each of the required molecular dynamics simulations, each such simulation being of a surfactant mixture 200 of a particular formulation k having a particular total surfactant concentration $c_t$ and particular mole fractions of each surfactant species $z_1, z_2 \ldots z_n$. The formulation k shown in this figure corresponds to any one of the simulation parameter sets 20 of FIG. 1. During each such simulation, surfactant molecules within a simulated volume 205 form micelles, shown in the volume 205 as a micellar pseudo-phase 212. Surfactant molecules not within micelles are then considered to be within a non-micellar pseudo-phase 214. Although these phases are shown as separate boxes within the simulated volume 205 in FIG. 2, the micelles and non-micellar (monomer and sub-micellar clusters) will of course be intermingled in the simulated volume.

At periodic intervals of the simulated time of each molecular dynamics simulation, the distribution analyser 215 determines a distribution D, within the simulated volume, of the surfactant molecules between the micellar and non-micellar pseudo-phases 212, 214. This can be achieved by defining one or more criteria for deciding if a molecule forms part of a micellar cluster, for example on the basis of proximity to other molecules, and the size of the resulting cluster. For any particular formulation of the mixture, this data can be averaged or otherwise combined over multiple such periodic intervals, and over multiple runs of the molecular dynamics simulation for that mixture.

The resulting distribution data provides, for each of plurality of different formulations k, a partition of each of the surfactant species 1 . . . n between a mole fraction x in the non-micellar pseudo-phase and a mole fraction y in the micellar pseudo-phase, so that D for each formulation k can be expressed as $D_k = [x_1, y_1, x_2, y_2, \ldots x_n, y_n]_k$ as shown in the figure.

This distribution data D is passed to the thermodynamics unit 16 which comprises a parameter fitting unit 230 and a property estimator unit 240, and a thermodynamics model 250. The thermodynamics model 250 of FIG. 2 is a pseudo-phase separation model (PSM) comprising an energy or PSM relationship 252 relating the critical micelle concentration $c_i^*$ of each particular surfactant species to the mole fractions of that species $x_i, y_i$ in each of the non-micellar and micellar pseudo-phases, which are known for particular formulations k from the molecular dynamics output distributions D.

The PSM relationship 252 for each species i may also involve the total surfactant concentration in the non-micellar and micellar pseudo phases $c_f, c_t$, which are related to the separate non-micellar and micellar pseudo-phase mole fractions $x_i$, $y_i$ through a mass balance relationship 254 of the thermodynamics model 250.

The PSM relationship for each species i also includes an activity coefficient $\gamma_i$ for that species, which expresses the degree to which that species deviates from ideal mixing behaviour within the micellar pseudo-phase. The thermodynamics model 250 therefore also comprises a set of mixing model relationships 256, which together form a Margules mixing model, Redlich-Kister model, or other non-ideal mixing model. Each mixing model relationship 256 defines an activity coefficient $\gamma_i$ in terms of non-ideal mixing parameters $A_1 \ldots A_m$, as well as in terms of the mole fractions of the surfactants in the micellar pseudo-phase $y_{1 \ldots i}$.

The non-ideal mixing parameters $A_1 \ldots A_m$ are then treated as constants of the mixing model, for the particular mixture of surfactants which is being considered irrespective of relative total proportions of the constituent species, and a function of the parameter fitting unit 230 is then to find optimum values of these non-ideal mixing parameters by fitting the thermodynamic model 250 to the distribution data D from the molecular dynamics simulations for the surfactant mixture. This can be achieved for example by using a least squares type fit where the best fit values for the non-ideal mixing parameters minimise a least squares function of differences between the non-micellar and micellar pseudo-phase mole fractions $x_i$, $y_i$ as determined by the molecular dynamics simulations and as predicted by the thermodynamics model 250.

Having determined optimum values for the non-ideal mixing parameters, the property estimator unit is then arranged to use these within the thermodynamic model 250 to estimate the critical micelle concentration c* for the mixture, and/or other properties which can be estimated using the thermodynamic model 250, at one or more different ratios of concentrations of the component surfactants. Other properties may include, for example, one or more estimates of ratios of the component surfactants which will give rise to corresponding one or more target critical micelle concentrations.

Figure 3A:
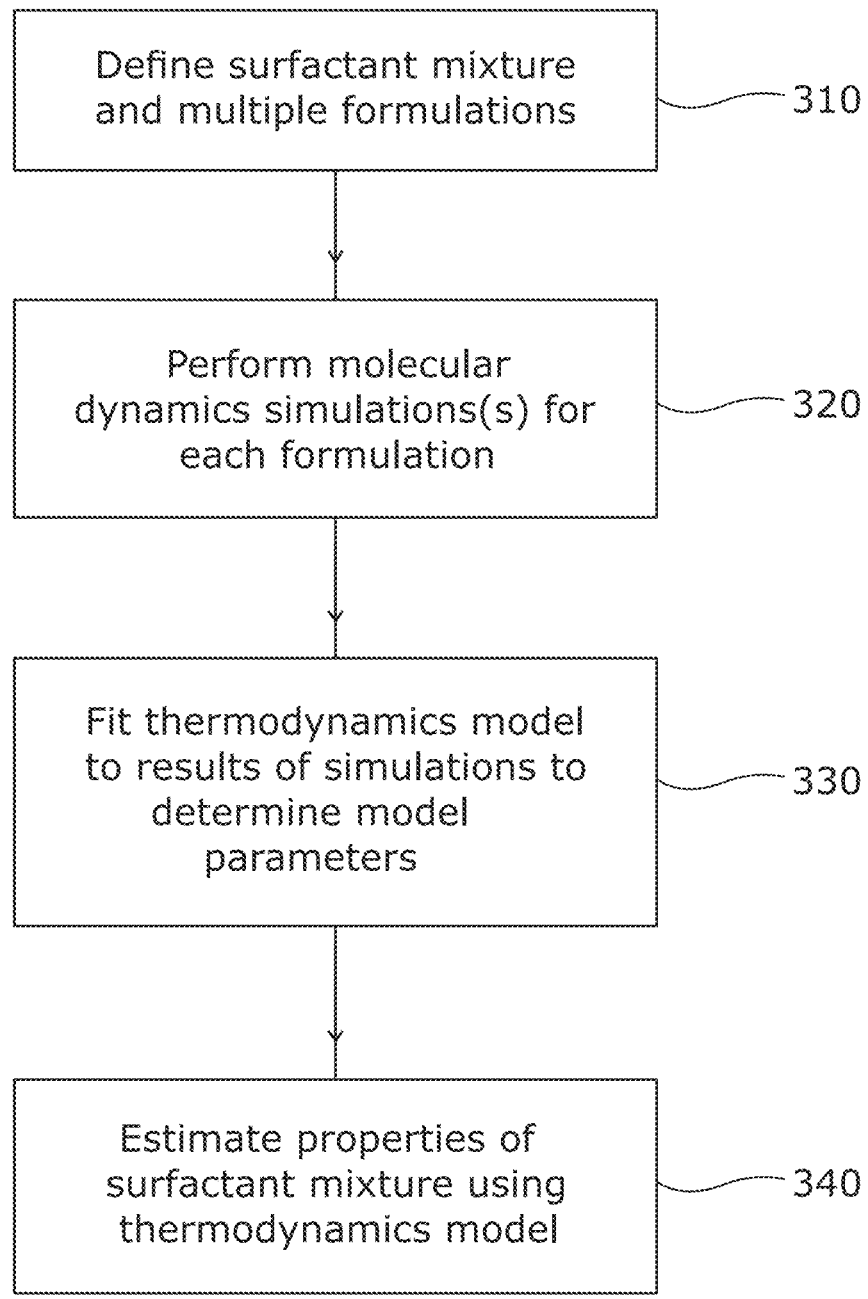
FIG. 3a illustrates a method of estimating properties of a mixture of surfactants using the apparatus of claim 1 or 2.

FIG. 3a illustrates methods which are carried out by operation of the apparatus of FIG. 1 or 2 to estimate one or more properties of a mix of surfactants. In step 310 a mix of two or more surfactant species is defined or chosen. A plurality of different formulations of that mix is also defined or chosen, with the formulations covering a range of different ratios of mole fractions of the multiple surfactant species, and a range of different total concentrations of surfactants. This plurality of formulations is illustrated by the simulation matrix 18 of FIG. 1. The plurality of formulations may include all of the defined ratios for each total concentration, or subsets of all possible combinations may be used. The number of different ratios used may typically be from about two to ten. The number of different total concentrations used may also typically be form about two to ten and ten. All of the formulations for simulation are above the relevant critical micelle concentration.

In step 320 one or more molecular dynamics simulations are performed for each formulation from step 310, for example using the molecular dynamics unit 14 of FIG. 1, and more particularly the molecular dynamics simulator 210 of FIG. 2. In this step, distributions of the modelled surfactant molecules are determined for example at each of a plurality of time points in each simulation, for example using the distribution analyser 215 of FIG. 2. The determined distributions may for example define the partition of each surfactant species between a non-micellar and a micellar pseudo-phase as discussed above and illustrated as pseudo-phases 214 and 212 in FIG. 2.

In step 330 results from the molecular dynamics simulations are used in order to fit a thermodynamic model, such as the thermodynamic model 250 of FIG. 2, to those results, to obtain fitted parameters of that model, for example using the parameter fitting unit 230 of FIG. 2. In particular, these fitted parameters may be non-ideal mixing parameters such as parameters $A_{1 \ldots m}$ shown in the mixing model relationships 256 of the thermodynamic model 250 in FIG. 2. In this fitting process, these parameters are optimized such that the differences between results from the simulations and the corresponding predictions of the thermodynamics model 250 are minimised, for example according to a least squares procedure.

In step 340, the thermodynamic model 250 with the fitted parameters is used to estimate one or more properties of the mix of surfactants, for example the critical micelle concentration at one or more different ratios of the surfactant species, or a ratio of concentrations of the surfactant species expected to give rise to a particular target critical micelle concentration.

Some or all of the above steps as illustrated in FIG. 3a may be carried out automatically and without human intervention, for example using computer apparatus as illustrated in FIGS. 1 and/or 2, although typically step 310 in which particular surfactant mix formulations are defined for use by the apparatus and in the method may be carried out by a scientist or operator and supplied for use in automatic implementation of the other steps. In other arrangements, at least steps 320 and 330 may be separately carried out using computer apparatus, but with user intervention between the steps for example in order to check and process the output of the molecular dynamics simulations before step 330 is carried out.

Figure 3B:
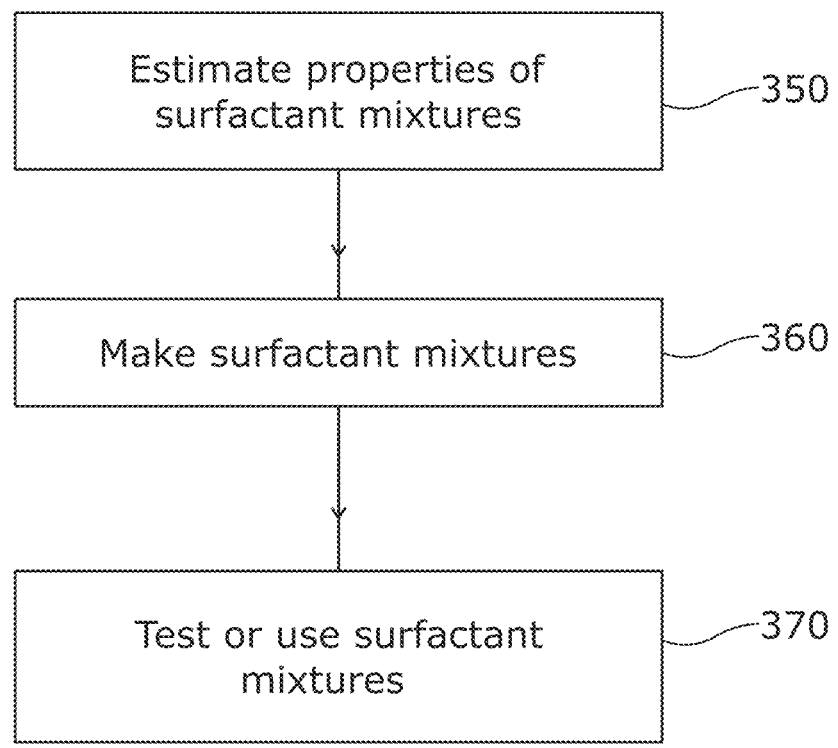

FIG. 3b illustrates how the method of FIG. 3a may be used to formulate and manufacture, and optionally also put into use, a surfactant mixture. Step 350 comprises the steps of the method illustrated in FIG. 3a, in which a mixture of surfactant species is simulated and modelled thermodynamically in different formulations in order to provide estimates of properties of the mixture such as critical micelle concentration at different ratios of mole fractions or other formulations of the component surfactants, or a ratio of surfactants required to achieve a particular target critical micelle concentration.

In step 360 a particular surfactant mixture is made or manufactured to be a mixture of the same surfactant species used in step 350. For example the mixture may be made up in a laboratory or manufactured in a factory or other industrial setting. Such a made up surfactant mixture may in particular have a ratio of the surfactant species which is expected to give rise, according to the thermodynamic model 250 and fitted parameters, to a particular target critical micelle concentration.

In step 370 the made surfactant mixture is tested, for example to determine whether it has desired or target properties, including for example the target critical micelle concentration, and/or is used for one or more intended purposes. Such a surfactant mixture may for example be used as or within a cosmetic product, a food or drink product, a cleaning product, a lubricant, a medicament, a paint, or any of a variety of other products where surfactant mixtures are used and where particular properties which can be estimated using the techniques described herein are considered important.

Methods of determining critical micelle concentration in a solution of a single surfactant species using computation arrangements such as those of FIGS. 1 and 2 as discussed above, will now be described in more detail. Sodium laureth sulfates (SLESs) are chosen as an exemplar of the problem, since this is a system which is both experimentally well characterised and of practical intrinsic interest.

Before moving on to discuss mixtures of surfactants, some general principles will first be introduced by describing the estimation of critical micelle concentration of each of a series of pure SLESn surfactant species with ethoxylate spacer lengths n=1, 2, 3, 5, and 10.

For each particular surfactant species, multiple molecular dynamics simulations were performed, using the techniques discussed in more detail below, at multiple total surfactant concentrations in the range $c_t$=30 to 75 mM, which concentrations are well above the CMC. The results of each simulation, in terms of physical distribution of individual surfactant molecules in 3D space of the model, were analysed using protocols previously developed for alkyl sulfate surfactants, for example see Anderson R L et al. (2018) "Micelle formation in alkyl sulfate surfactants using dissipative particle dynamics", J. Chem. Theory Comput. 14:2633:2643, which is hereby incorporated by reference for these and all other purposes.

More specifically, at a series of well-spaced time intervals, cluster analysis, of the individual surfactant molecules in 3D space, was used to build an aggregation number distribution, which was split to distinguish between (i) monomers and sub-micellar aggregates (a non-micelle pseudo-phase), and (ii) true micelles (a micelle pseudo-phase). The total concentration of surfactants in the former class was then block-averaged to obtain an estimate of the equilibrium notional 'monomer' non-micelle pseudo-phase surfactant concentration $c_f$ at a given total concentration of the surfactant species $c_t$, and therefore a distribution of the surfactant species between the micelle pseudo-phase ($c_t$–$c_f$) and the non-micelle pseudo-phase ($c_f$), represented in terms of concentrations.

For each total concentration $c_t$, the CMC was then estimated using a thermodynamics model, for example as discussed in Bates B L (2001), "A definition of the degree of ionization of a micelle based on its aggregation number", J. Phys. Chem. B 105:6798:6804, which is hereby incorporated by reference for these and all other purposes, and in particular using the thermodynamics phase separation model derived expression:

$$\ln c_f + \beta \ln\left(\frac{\beta c_f + (1-\beta)c_t}{1-\phi}\right) = (1+\beta)\ln c^* \quad (1)$$

where c* is the CMC, $\beta$ is a parameter giving the degree of ion binding, and $\varphi$ is the total surfactant packing fraction. For the former, $\beta$=0.7 was adopted following Anderson (2018) above, and for the latter we set $\varphi=V_m c_t$, where $V_m$ is the surfactant molar volume, computed assuming the density is 1 g/cc.

The factor $1/(1-\varphi)$ in equation (1) empirically accounts for the crowding effect of the surfactant on the unassociated counterions (the numerator in the above expression, see Bates B L (2001) above. Note that the model predicts $c_f$ decreases with increasing $c_t$>c*. This effect derives from the counterions and can be viewed as the analogue of the common-ion effect in the solubility of sparingly-soluble salts.

Figure 4A:
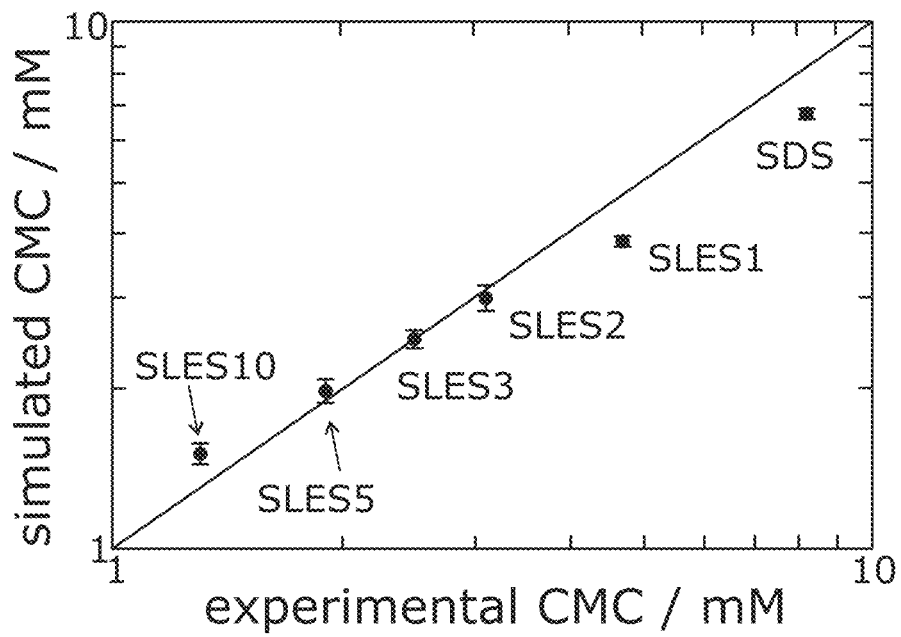
FIG. 4a plots experimentally determined critical micelle concentration of various single surfactants against critical micelle concentration estimated using molecular dynamics and PSM modelling.

As shown in FIG. 4a, the CMCs thus estimated, averaged over replicate runs of the molecular dynamics model and multiple different total surfactant concentrations, show very good agreement with experimental results for pure single-component SLES surfactants. In particular, FIG. 4 shows the estimated CMC values for the surfactant species SDS and each of the five SLESn species mentioned above, plotted against laboratory experimental values. This is viewed as confirmation of the accuracy of the molecular dynamics simulation used (including the coarse-grained model molecular fragmentation strategy and the associated force-field parameters discussed below). It can be seen that there is a general trend for the CMC to decrease with increasing ethoxylate spacer length, from around 7 mM for n=0 (SDS) to around 1-2 mM for n>5. This can be attributed to the lowered electrostatic free energy cost of forming micelles if the charged head groups can lie further away from the hydrocarbon core.

Following the general strategy outlined above, methods of determining critical micelle concentration in a solution of multiple surfactant species using computation arrangements such as those of FIGS. 1 and 2, will now be described in more detail, starting with binary mixtures of the surfactants discussed above, and focusing first on the SLES1/SLES3 combination. To this end, molecular dynamics simulations were carried out, using the techniques discussed in more detail below, at multiple total surfactant concentrations in the range 30 to 75 mM, and at a multiple different ratios of the two surfactant species, in particular exploring mole ratios 1:1, 1:3, and 3:1 of SLES1:SLES3.

The same cluster or distribution analysis, of the individual surfactant molecules in 3D space, as for the single-component systems described above was then used at a series of well-spaced time intervals of the molecular dynamics model, to build an aggregation number distribution, except that of course one can now also trivially resolve the compositions (in terms of proportion of each surfactant species) in the non-micellar ("monomer") and micellar surfactant pseudo-phases. With the total surfactant concentration in the non-micellar pseudo-phase again being represented by $c_f$, the mole fraction of the i-th surfactant species in the non-micellar and the micellar pseudo-phases respectively can be denoted $x_i$ and $y_i$.

Figure 4B:
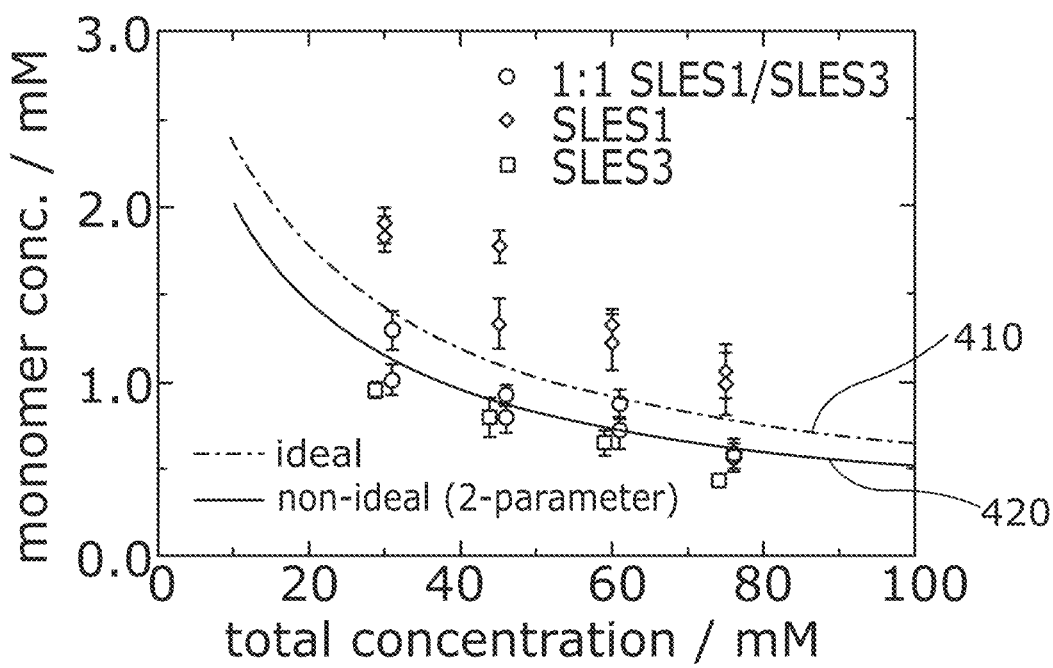
FIG. 4b plots overall monomer concentration in an SLES1/SLES3 mixture molecular dynamics simulation against total concentration (round points), as well as for corresponding single surfactant solutions (diamond and square points), with curves showing the same for the SLES1/SLES3 mixture as calculated using fitted thermodynamics models using an ideal mixing model (broken) and a 2 parameter non-ideal mixing model (solid). The lower points are jittered to avoid overplotting.

FIG. 4b plots results of these simulations in terms of the total concentration of surfactants $c_f$ in the non-micellar pseudo-phase for a binary mix of SLES1 and SLES3 with a 1:1 total ratio ("○" points). Also shown above and below the points for the binary mix are corresponding concentrations for simulations of single surfactant solutions of SLES1 and SLES3 respectively (diamond and square points respectively), showing that the total non-micellar pseudo-phase concentration of the binary mix lies between those of the two pure systems, but is much closer to that of SLES3 than SLES1, and clearly below the expectation assuming ideal mixing in the micelles which is shown by the central broken line 410. In other words there is an enhanced tendency to form micelles in the mixed system, according to the molecular dynamics simulations. The solid line 420 shows a fit to the non-ideal mixing two parameter thermodynamics model discussed further below.

Figure 4C:
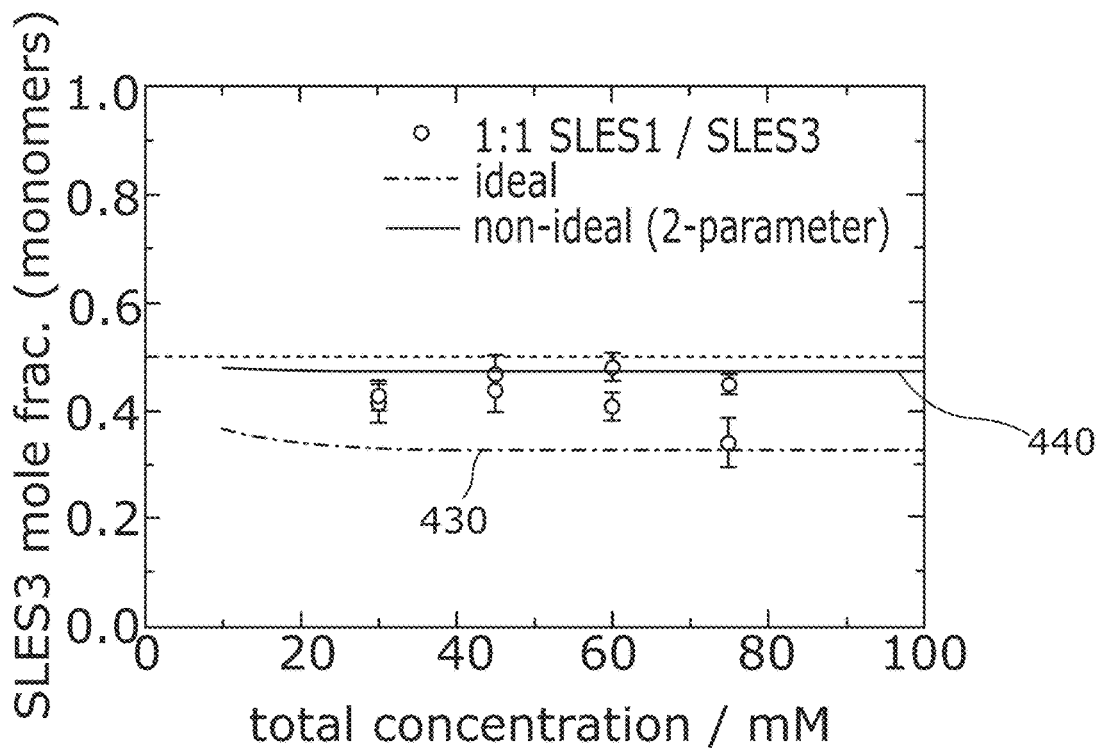
FIG. 4c plots modelled SLES3 monomer mole fraction against total surfactant concentration in a 1:1 SLES1/SLES3 mixture, resulting from a molecular dynamics simulation (points), with curves showing the same using fitted thermodynamics models using various mixing models.
Figure 4D:
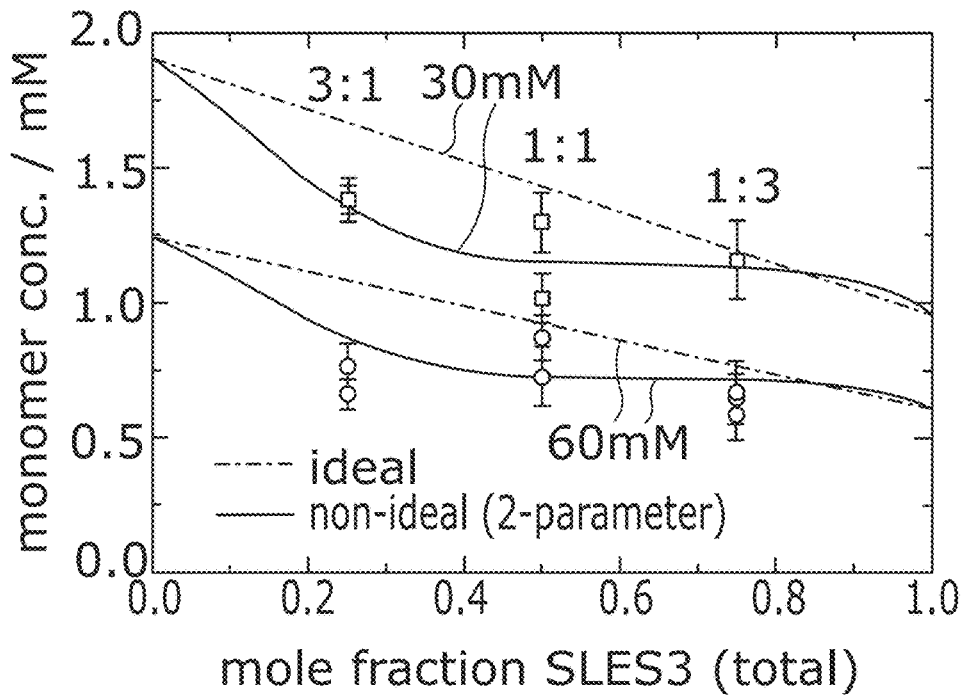
FIG. 4d plots total monomer concentration as a function of mole fraction of SLES3 in SLES1/SLES3 mixtures, at the indicated overall concentrations.

FIG. 4c illustrates results of the molecular dynamics simulations in terms of mole fractions of SLES3 in the non-micellar pseudo-phase (so $x_2$ if SLES3 is a second species) as a function of total surfactant concentration $c_t$ for a SLES1/SLES3 mixture at 1:1 mole ratio. It can be seen that the composition of the non-micellar pseudo-phase is slightly enriched in SLES1 (in a vapour-liquid equilibrium analogy, this is the more volatile component, corresponding to the higher CMC) but not to the extent that would be predicted by ideal mixing as shown by curve 430. Curve 440 shows the fit to a non-ideal 2-parameter mixing model as discussed below.

FIG. 4d again illustrates results of the molecular dynamics simulations in terms of total non-micellar pseudo-phase concentration $c_f$ as a function of the ratio or mole fraction of SLES3 in SLES1/SLES3 mixtures, at the indicated total overall concentrations $c_t$. These non-micellar pseudo-phase concentrations show significant deviations from ideal mixing at a 3:1 mole ratio (25% SLES3), but much less so at a 1:3 mole ratio (75% SLES3). This study was repeated replacing SLES3 by SLES5, finding very similar trends.

It can be concluded from these results that despite comprising surfactants which are near-neighbours in a homologous series, these binary mixtures deviate from ideal mixing, exhibiting a modest degree of co-operativity in the formation of mixed micelles. This can be attributed to a reduced repulsion between the charged head groups, which can now not only be spaced away from the hydrocarbon core (cf. the CMC trend for pure SLES systems) but also spaced away from each other in a mixed micelle due to the difference in ethoxylate spacer lengths. Additionally, the non-ideality is skewed towards enriching micelles in the surfactant with the shorter ethoxylate spacer (i.e. SLES1).

Results from the molecular dynamics simulations, including distribution of each surfactant species between the non-micellar and the micellar pseudo-phases, as well as the total non-micellar pseudo-phase concentration, are then used to fit parameters of a thermodynamics model, and in particular a pseudo-phase separation model (PSM). The PSM and the fitted parameters can then be used to estimate the CMC and/or other properties of the simulated mixture, at any of a range of ratios of the mixed surfactant species.

In particular, this can be achieved by adopting and extending the thermodynamics models described for example in Kamrath R F and Franses E I (1986) "*New mathematical models of mixed micellization*", Phenomena in Mixed Surfactant Systems, ACS Symposium Series vol 311, ed. Scamehorn J F, pp 44-60, which is hereby incorporated by reference for these and all other purposes. A starting point is the generalisation of equation (1) above to a multicomponent mixture of like-charged ionic and nonionic surfactants:

$$\ln x_i c_f + \beta_i \ln\left(\frac{\beta c_f + (q-\beta)c_t + c_s}{1-\phi}\right) = \ln y_i \gamma_i + (1+\beta_i)\ln c_i^* \quad [2]$$

In this equation, $x_i$ and $y_i$ are the mole fractions of the i-th surfactant species in the non-micellar and the micellar pseudo-phases respectively, $\beta_i$ is a species-specific ion binding parameter, $\beta = \Sigma_i \beta_i y_i$ is the weighted mean, $q = \Sigma_i q_i z_i$ accounts for counterions contributed by surfactants at valency $q_i$ (i.e. $q_i$=0 for nonionics, $q_i$=1 for ionics, where $z_i$ is the overall mole fraction), $y_i$ is the activity coefficient for the i-th species in the micellar pseudo-phase, $c_i^*$ is the CMC of the i-th component, and $c_s$ is the concentration of added salt which is included for generality. Other quantities have the same meaning as in equation (1).

Equation 2 represents a pseudo-phase separation model that generalises the binary mixture pseudo-phase separation model presented by Kamrath and Franses (1986), except that for simplicity it is assumed that the degree of ion binding is linear in the micelle composition. With a suitable thermodynamic model for the activity coefficients together with mass balance in the form $z_i c_t = x_i c_f + y_i (c_t - c_f)$, equation (2) can be solved numerically for the non-micellar pseudo-phase concentration $c_f$, and the non-micellar and micellar pseudo-phase compositions of each species i which are $x_i$ and $y_i$ respectively, in other words the distribution of each surfactant species between the two pseudo-phases. For the SLES surfactant systems discussed here it can be assumed $\beta_i$=0.7 for all surfactants.

The activity coefficient $\gamma_i$ for each surfactant species may be represented using standard sub-models for the excess mixing free energy per surfactant $g^{ex}$ in the micellar pseudo-phase. For binary systems a two-parameter Margules model may be used, with $g^{ex} = y_1 y_2 (A_1 y_1 + A_2 y_2)$. This is functionally equivalent to the Redlich-Kister series expansion truncated after the second term, and for $A_1 = A_2$ reduces to regular solution theory (one-parameter Margules model). For multicomponent mixtures a generalized non-ideal mixing model may be used such as $g^{ex} = \Sigma_{i>j} A_{ij} y_i y_j$. For a binary system, this also reduces to regular solution theory which establishes a bridge between the two approaches. Expressions for the corresponding activity coefficients are given in the discussion of activity coefficients below. The parameters $A_i$ of the mixing model can be referred to as mixing parameters, or more specifically where the model is for non-ideal mixing, non-ideal mixing parameters.

Figure 5A:
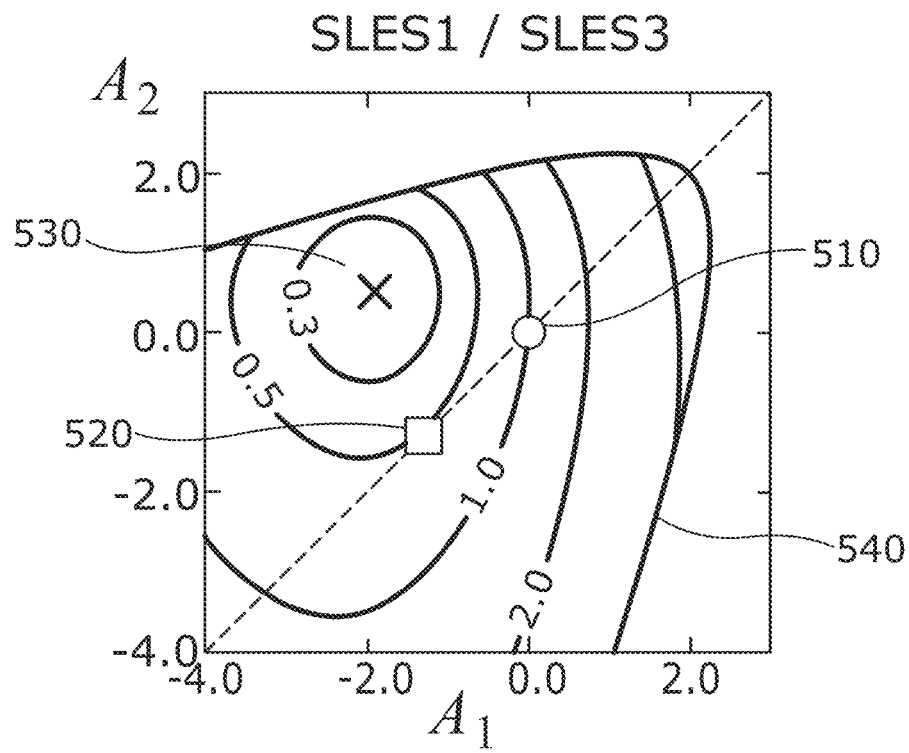
FIGS. 5a and 5b show contours of least squares objective function fits of non-ideal mixing (Margule model) parameters in a thermodynamic model to distribution data from molecular dynamics simulations for two different surfactant mixtures.
Figure 5B:
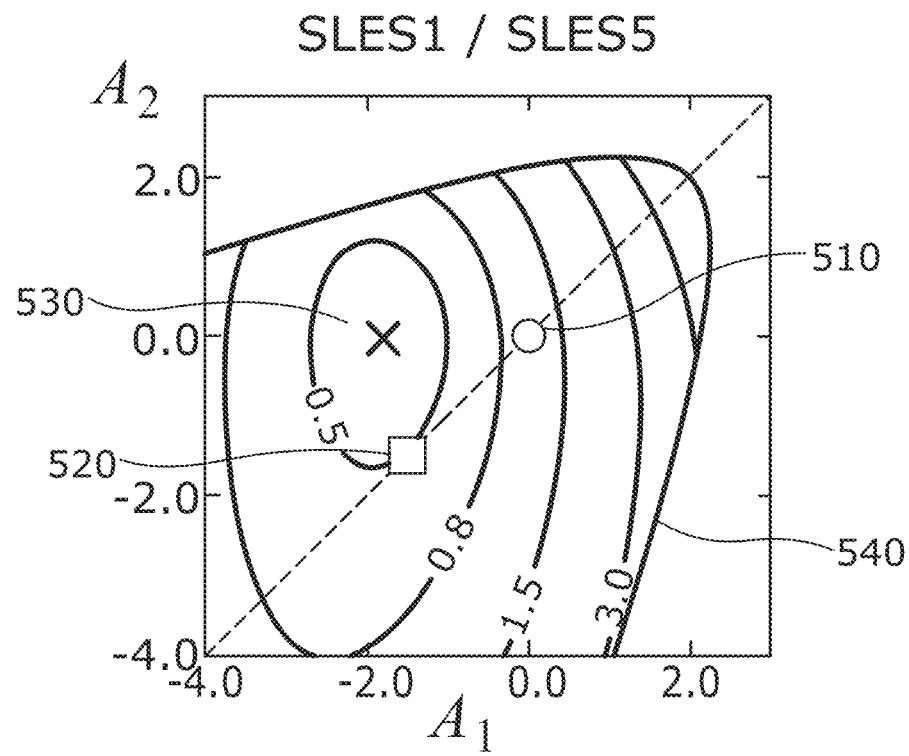

A least-squares (LS) fitting procedure may be used to fit the mixing parameters, where the LS objective function is the sum of the squares of the deviations of the predicted non-micellar pseudo-phase concentrations for each surfactant species (i. e. $x_i$ $c_f$) from the simulation results. The results of this fit to the two parameter Margules model outlined above is shown for an SLES1/SLES3 mixture in FIG. 5a and for an SLES1/SLES5 mixture in FIG. 5b. Also shown in these figures are the ideal mixing point 510 ($A_1 = A_2 = 0$) depicted as a "○" point where, and a best fit point 520 for a single parameter model ($A_1 = A_2$) depicted as a "□" point. The optimum two parameter non-ideal mixing fit 530 is shown as point "x". The boomerang shaped envelopes 540 show the limits of thermodynamic stability of the micellar pseudo-phases given by equation (5) below.

Figure 5C:
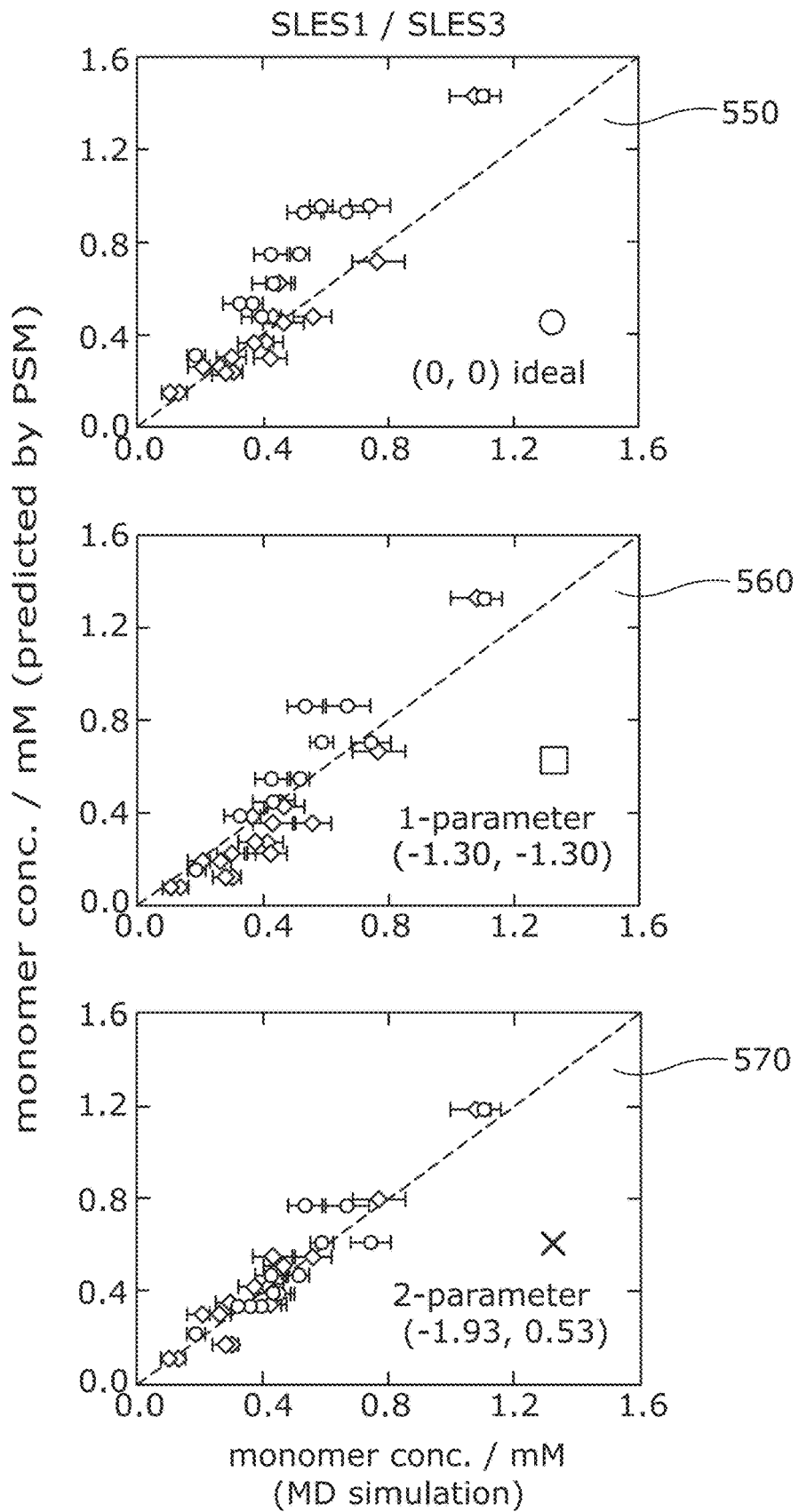
FIG. 5c shows individual surfactant monomer concentrations for the SLES1/SLES3 system, comparing molecular dynamics simulation (abscissa) with thermodynamics model prediction (ordinate) for ideal (top), one parameter (middle) and two parameter (lower) mixing models.

It can be seen from these figures that the objective fitting function is relatively smooth in the ($A_1$, $A_2$) non-ideal mixing parameter plane. FIG. 5c shows individual surfactant species concentrations in the non-micellar pseudo-phase, as output by the molecular dynamics model plotted against that calculated using the PSM approach of equation (2). SLES1 concentrations are shown as circles, and SLES3 as diamonds. In the top panel 550 of the figure the PSM calculation used the ideal mixing assumption of $A_1 = A_2 = 0$, in the middle panel 560 the PSM calculation used the single parameter fit to the simulation output such that $A_1 = A_2$, and in the lower panel 570 the PSM calculation used the full two parameter fit non-ideal mixing model. It can be seen that relaxing from the assumption of ideal mixing to a one- then a two-parameter LS fit sharpens up the PSM predictions compared to the molecular dynamics simulation. The fitted non-ideal mixing parameters for both this and the SLES1/SLES5 system are reported in Table 1 below.

TABLE 1

| Mixture | $A_1$ | $A_2$ | $A_1 = A_2$ |
|---|---|---|---|
| SLES1/SLES3 | −1.9 ± 0.1 | +0.5 ± 0.1 | −1.3 ± 0.1 |
| SLES1/SLES5 | −1.8 ± 0.3 | −0.1 ± 0.3 | −1.5 ± 0.3 |

These results quantify the degree of co-operativity in the formation of mixed micelles, and are numerically similar to those tabulated in the literature for anionic/nonionic surfactant mixtures. An advantage of adopting an LS approach is that it can be restricted to the $A_1=A_2$ sub-space to obtain an unbiased, optimised estimate of the regular solution parameter A in a one-parameter Margules model, which can be used to feed the $A_{ij}$ in a multicomponent non-ideal mixing model.

We now turn to the calculation of critical micelle concentration following fitting of the mixing parameters. As we have alluded to above, this is already contained in the PSM as the limit $c_t \to c_f$ where there is a vanishingly small amount of surfactant in micelles. In this limit equation 2 above yields:

$$\ln x_i c^* + \beta_i \ln(qc^* + c_s) = \ln y_i \gamma_i + (1+\beta_i) \ln c_i^*. \quad [3]$$

It is then assumed that the overall concentration is small so that $\varphi \ll 1$ and the molecular crowding correction can be neglected. Solving equation 3 gives the CMC of the mixture ($c^*$), and the composition of the first-formed micelles ($y_i$), as a function of the overall composition ($x_i$) including if desired the effect of added salt at a concentration $c_s$. Note that equation 3 becomes an identity for a pure component in the absence of salt since the activity coefficients $\gamma_i \to 1$ in the micellar pseudo-phase for the concentrations in the micellar pseudo-phase $y_i \to 1$.

Figure 6A:
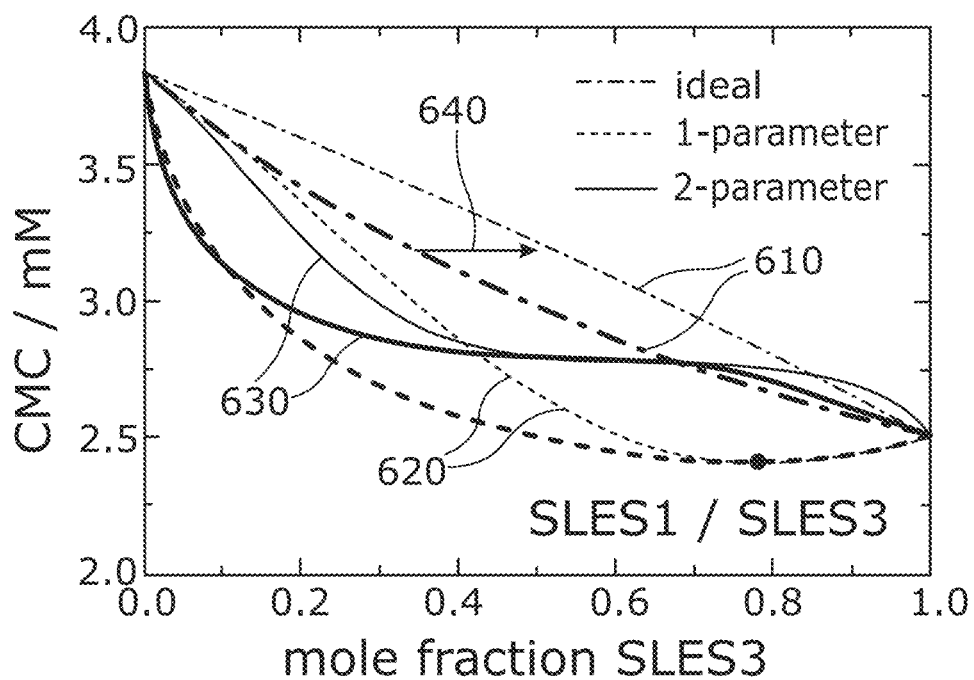
FIG. 6a plots estimated critical micelle concentrations for a binary SLES1/SLES3 mixture, against total mole fraction of SLES3, for three different mixing models.

As an example of this, FIG. 6a shows the CMC (heavier lines) and composition of the first-formed micelles (lighter lines) for a binary SLES1/SLES3 mixture, calculated by solving equation (3) using the ideal, one-, and two-parameter Margules mixing models fitted from the molecular dynamics simulations (the mixing parameters of Table 1). It can be seen that generally the CMC is depressed below the ideal mixing case as a consequence of the co-operativity of mixed micelle formation in this system. For the one-parameter Margules model, the CMC even exhibits a minimum as a function of composition, at which point the first-formed micelles have the same composition as the bulk so this is the analogue of a vapour-liquid equilibrium azeotrope. It is possible in principle for the population of mixed micelles to demix in some range of compositions (quite likely accompanied by bulk phase separation), if the micellar pseudo-phase is thermodynamically unstable. However, this is not seen in the present models since the LS optima all lie within the region of thermodynamic stability (envelopes 520 seen in FIGS. 5a and 5b).

The CMC and the solution state at concentrations above the CMC are readily solved for a general m-component PSM by introducing m independent, unbounded, derived variables $u_i$. For example this derived variable can be used: $u_i = \ln(x_i c_t / c_t - 1)$ for equation (2), and $u_i = \ln(y_i / c^*)$ for equation (3). The least-squares (LS) fitting can be approached by constructing a wrapper around a solution state solver to use with the LS package available from the SciPy community, for example see https://www.scipy.org/about.html. In particular, an unweighted LS objective function can be used since the standard errors determined by the block-averaging procedure are noisy and uncertain but mostly all of a similar magnitude. The spread in the fit parameters indicated in Table 1 above was estimated by LS fitting the PSM to 20 random subsets of the simulation data, each of size N=20 data points (cf. jackknife subsampling). Numerical codes for these purposes may be built for example on the NumPy and SciPy libraries described in van der Walt S, Colbert S C, Varoquaux G (2011) "The NumPy array: A structure for efficient numerical computation", *Comput. Sci. Eng.* 13:22-30, and Virtanen P, et al. (2020) "SciPy 1.0: Fundamental Algorithms for Scientific Computing in Python", *Nat. Methods* 17:261-272, which is hereby incorporated by reference for these and all other purposes.

Molecular Dynamics Model Discussion

The molecular dynamics simulations used in the detailed examples above use coarse-grained models based on the dissipative particle dynamics (DPD) simulation methodology set out in Español P and Warren P B (2017) "Perspective: dissipative particle dynamics", *J. Chem. Phys.* 146:150901, which is hereby incorporated by reference for these and all other purposes. The fragmentation strategy maps chemical groups containing 1-3 'heavy atoms' (C, O, S) onto DPD beads, with the exception of water which is treated super-molecularly ($2 \times H_2O$). Electrostatic interactions are incorporated using smeared charges for the ionic headgroup and the hydrated counterion, with the latter being a charged water bead. The force-field parameters for the bonded and non-bonded interactions has been validated for the CMCs of alkyl ethoxylate and alkyl sulfate surfactants—see Anderson R L, et al. (2017) "Dissipative particle dynamics: systematic parametrization using water-octanol partition coefficients", *J. Chem. Phys.* 147:094503, and Anderson R L, et al. (2018) "Micelle formation in alkyl sulfate surfactants using dissipative particle dynamics", J. Chem. Theory Comput. 14:2633-2643—and most recently used to probe micellar morphologies in supra-micellar SLES solutions—see Panoukidou M, Wand C R, Del Regno A, Anderson R L, Carbone P (2019) "Constructing the phase diagram of sodium laurylethoxysulfate using dissipative particle dynamics", *J. Colloid Interf. Sci.* 557:34-44, all of which are hereby incorporated by reference for these and all other purposes. Force-field parameters as described in this last publication were used.

The Molecular dynamics simulations were carried out under constant-pressure conditions, using the DL_MESO simulation engine described in Seaton M A, Anderson R L, Metz S, Smith W (2013) "DLMESO: highly scalable mesoscale simulations", *Mol. Simul.* 39:796-821, which is hereby incorporated by reference for these and all other purposes, with a Langevin-piston barostat (P=23.7 in reduced units), particle-mesh Ewald for the electrostatic interactions, and a time step $\Delta t=0.01$ in reduced units. All simulations comprised $10^3$ surfactant molecules made up to volume by water beads to obtain the desired total concentration. The conversion to molar concentrations was done using the length scale $r_c=0.565$ nm, defined by the water bead 'mapping number' ($N_m=2$) as explained in Anderson R L, et al. (2017) "Dissipative particle dynamics: systematic parametrization using water-octanol partition coefficients", *J. Chem. Phys.* 147:094503, which is hereby incorporated by reference for these and all other purposes.

Each molecular dynamics simulation was typically run for $9 \times 10^6$ time steps, with the configurations of the modelled particles sampled to determine distributions of surfactant species between the micellar and non-micellar pseudo-phases every 2000 time steps, where the non-micellar pseudo-phase comprises monomer plus sub-micellar aggregate components. These distributions were sampled as concentrations in each pseudo-phase from the simulation trajectories using the UMMAP post-simulation analysis package described in Bray D J, Regno A D, Anderson R L (2020) "UMMAP: a statistical analysis software package for molecular modelling", *Mol. Simul.* 46:308-322, which is hereby incorporated by reference for these and all other purposes, with the same clustering criteria as described for the alkyl sulfate surfactants (see Anderson R L et al. 2018 above).

The first $4 \times 10^6$ time steps of each molecular dynamics simulation was discarded as equilibration, and block-averaging was used (block size $10^6$ time steps; 4-5 blocks per simulation) on the remainder to obtain the mean concentrations and compositions, and estimate the standard errors thereof.

Activity Coefficients Detail

The activity coefficients corresponding to the binary mixture two-parameter Margules mixing model can be expressed as $\ln \gamma_1=[A_2+2(A_1-A_2)y_1]y_2^2$ and $\ln y_2=[A_1+2(A_2-A_1)y_2]y_1^2$ for example see Walas S M (1985) "Phase Equilibria in Chemical Engineering", (Butterworth, Stoneham, MA), which is hereby incorporated by reference for these and all other purposes. For $A_1=A_2=A$ this reduces to regular solution theory with $\ln \gamma_1 = A y_2^2$ and $\ln \gamma_2 = A y_1^2$. For the multicomponent mixing model the activity coefficients are:

$$\ln \gamma_i = 2\Sigma_{j>i} A_{ij} y_j - \Sigma_{j,k>j} A_{jk} y_j y_k \quad [4]$$

In reconciling these expressions with the literature (see Holland P M and Rubingh D N (1983) "Nonideal multicomponent mixed micelle model", *J. Phys. Chem.* 87:1984-1990, which is hereby incorporated by reference for these and all other purposes), recall that $\Sigma_i y_i = 1$. Note that in regular solution theory at $y_1 = y_2 = \frac{1}{2}$, the activity coefficients obey $\ln \gamma_1 = \ln \gamma_2 = A/4$. This peculiarity means that at 1:1 micellar mole ratio the monomer composition becomes insensitive to A, shown for example in FIG. 4c. Since we typically run the molecular dynamics simulations at a total surfactant concentration greatly in excess of the CMC where the mass balance is dominated by micelles ($y_i \approx z_i$), it is relatively easy to use this as a litmus test for deviations from regular solution theory.

For thermodynamic stability in the binary mixture we require $d^2g/dy^2 \geq 0$ (see Kamrath R F, Franses E I (1983) "Thermodynamics of mixed micellization. pseudo-phase separation models" *Ind. Eng. Chem. Fundam.* 22:230-239), which is hereby incorporated by reference for these and all other purposes, where $g(y) = y \ln y + (1-y) \ln(1-y) + g^{ex}$ and $y_2 = 1 - y_1 = y$ should be substituted in the expression for $g^{ex}$. The stability boundary (envelopes 520 in FIGS. 5a and 5b) can be expressed parametrically as a function of $0 < y < 1$ by solving $d^2g/dy^2 = d^3g/dy^3 = 0$, as $$A_1 = \frac{-9y^2 + 8y - 1}{6y^2(1-y)^2}, \quad [5]$$

$$A_2 = \frac{-9y^2 + 10y - 2}{6y^2(1-y)^2}.$$

Application Example

The approach above can also be used to estimate one or more properties of a mixture of surfactants which comprise both the surfactant species which are the subject of the molecular dynamics simulations and the thermodynamic model fitting described above, and one or more further surfactant species.

In particular, the power of the present approach can be demonstrated by solving equation (3) for polydisperse SLES blends. By way of example the question raised in the introduction about the possible origins of the reduced CMC in a commercial SLES2 can be addressed. For simplicity we adopt a rudimentary model for the distribution of ethoxylate spacers in a polydisperse mixture, working with our current set of spacer lengths n=1, 2, 3, 5, 10 and assuming these are present in the mixture in mole ratios a:1:b:b:b. By setting a/b=1942/83 we anchor the weight-average molecular weight at the value MW=376 for pure SLES2 (we assume the individual molecular weights are $M_i$=288+44n). We now solve equation (3) to find the CMC in the blend as a increases from zero, trying various meta-models for the $A_{ij}$ mixing parameters motivated by the results in Table 1.

Figure 6B:
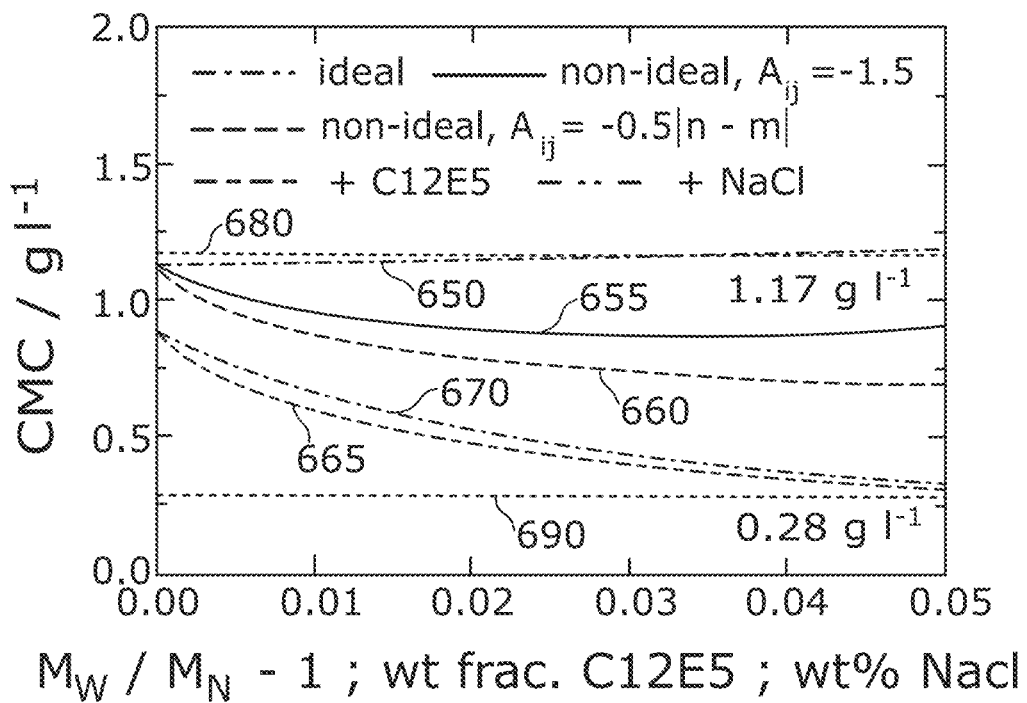
FIG. 6b plots the estimated critical micelle concentration of a polydisperse SLES2 surfactant blend with $C_{12}E_5$, as a function of the weight fraction of the latter.

FIGS. 6a and 6b illustrate some CMCs calculated for SLES mixtures using the techniques described above. FIG. 6a shows a binary SLES1/SLES3 system assuming ideal mixing (curves 610), and for one- and two-parameter best-fit Margules mixing models (curves 620 and 630 respectively). The heavier lines are the CMC as a function of the mole fraction of SLES3 and the lighter lines represent the composition of the first-formed micelles, as indicated by the arrow 640 for the ideal case. These lines are the analogue of the dew and bubble point curves respectively in a vapor-liquid equilibrium (VLE). For the one-parameter case the minimum of the CMC curve (marked point) is where the first-formed micelles have the same composition as the overall solution, analogous to an azeotrope in VLE.

FIG. 6b plots the CMC of a polydisperse SLES2 blend, expressed in g l$^{-1}$, as a function of the polydispersity index (with MW=376 fixed), for various mixing free energy models, including: ideal (labelled as curve 650); non-ideal (labelled as curve 655) with $A_{ij}$=−1.5; and non-ideal (labelled as curve 660) with $A_{ij}$=−0.5|n−m|. Also shown is the CMC (curve 665) for a blend of polydisperse SLES2 and the alkyl ethoxylate surfactant $C_{12}E_5$ representing an unsulfated minority component, as a function of the weight fraction of the latter; and the CMC (curve 670) for polydisperse SLES2 plus salt (NaCl), as a function of the weight percent salt. The CMCs of pure SLES2 (1.17 g l$^{-1}$, upper dotted line 680) and a commercial material STEOL CS-270 (0.28 g l$^{-1}$, lower dotted line 690).

FIG. 6b therefore shows two cases of solutions to the PSM for the polydisperse blend, first in curve 655 for a uniform model with $A_{ij}$=−1.5, and second in curve 660 for a graded model with $A_{ij}$=−0.5|n−m| where n and m are the lengths of the ethoxylate spacers. We plot the CMC in g l$^{-1}$ (if c* is in mM this is given by $\Sigma_i 10^{-3} M_i x_i c^*$) as a function of the degree of polydispersity $M_W/M_N$ (where $M_N = \Sigma_i M_i x_i$). Note that in the adopted model, the maximum $M_W/M_N \approx 1.05$ (for a>>1). The results clearly show that polydispersity in the ethoxylate spacer length lowers the CMC, for the same reason as in the binary mixture (FIG. 6a). However, in the present model at least, this is insufficient to explain the four-fold reduction seen in the CMC for the commercial material.

This compels us to investigate other possible explanations. First, it is always possible that unsulfated material is present which would drive down the mixture CMC by virtue of having a much reduced CMC itself. To demonstrate this, we investigated the effect of including a small amount of an alkyl ethoxylate, penta-ethylene glycol monododecyl ether ($C_{12}E_5$), as a 'toy' model. This is a nonionic surfactant with chemical formula $CH_3(CH_2)_{11}(OCH_2CH_2)_5OH$, molecular weight $M_i$=406, and $c_i^*$=0.065 mM or 0.026 g l$^{-1}$ (see Holland P M, Rubingh D N (1983) "Nonideal multicomponent mixed micelle model", *J. Phys. Chem.* 87:1984-1990). We add this to an already-polydisperse SLES with $M_W/M_N$=1.01 (c*=0.87 g l$^{-1}$), and solve the PSM in equation (3) with $\beta_i = q_i = 0$ for $C_{12}E_5$, assuming $A_{ij}$=−2 for the interaction with SLES (see Holland P M (1986) "Nonideal mixed micellar solutions", *Adv. Colloid Interf. Sci.* 26:111-129). We do now manage to get the mixture CMC down to the reported value of around 0.3 g l$^{-1}$, with ≈5 wt % $C_{12}E_5$ (FIG. 6*b*). We note however that the first-formed micelles in such a system would be highly enriched in the alkyl ethoxylate minority species (as the least-soluble component), which may have observable consequences although tricky to measure directly. Second, we can also reduce the CMC by having $c_s>0$ in equation (3). Again, a calculation with the PSM reveals that only trace amounts of salt (e. g. 0.05 wt %, or 0.5 g/kg NaCl) can have quite a dramatic effect (FIG. 6*b*). Thus we conclude that whilst the inevitable polydispersity in ethoxylate spacer length does likely contribute to the reduced CMC seen in a commercial SLES, other factors such as the presence of small amounts of unsulfated material and trace amounts of salt, or a combination, are more plausible explanations.

Although specific embodiments of the invention have been described with reference to the drawings, the skilled person will be aware that variations and modifications may be applied to these embodiments without departing from the scope of the invention defined in the claims.

For example, embodiments may include a method of estimating one or more properties of a mixture of two or more surfactant species, comprising: performing a plurality of molecular dynamics simulations of the mixture, each simulation using a particular total concentration of the surfactant species and a particular ratio of the surfactant species, such that the plurality of simulations cover a plurality of such total concentrations and a plurality of such ratios, each simulation being carried out above the critical micelle concentration of the simulated mixture; determining, for each simulation, and from the results of each simulation, a distribution of each surfactant species between at least a micellar pseudo-phase and a non-micellar pseudo-phase of the mixture at the particular total concentration and particular ratio for that simulation; fitting a thermodynamic model of the mixture to the distributions to determine fitted parameters of the thermodynamic model; and estimating the one or more properties using the thermodynamic model and the fitted parameters. In an alternative embodiment, the method may include wherein the one or more properties comprise the critical micelle concentration of the mixture at one or more ratios of the surfactant species. In an alternative embodiment, the method may include any preceding embodiment wherein the one or more properties comprise a ratio of the two or more surfactant species estimated to provide the mixture with a target critical micelle concentration. In an alternative embodiment, the method may include any preceding embodiment, wherein the one or more properties comprise one or more properties of a mixture of surfactants comprising the two or more surfactant species, and one or more further surfactant species. In an alternative embodiment, the method may include any preceding embodiment wherein the thermodynamic model comprises a pseudo-phase separation model (PSM). In an alternative embodiment, the method may include any preceding embodiment wherein the fitted parameters comprise a plurality of non-ideal mixing parameters representing mixing of the two or more surfactant species in the micellar pseudo-phase, the non-ideal mixing parameters being used in the thermodynamic model to determine an activity coefficient for each surfactant species within the micellar pseudo-phase. In an alternative embodiment, the method may include wherein the non-ideal mixing parameters are constants, for the mixture of surfactant species, of a Margules model or other non-ideal mixing model incorporated within the thermodynamic model. In an alternative embodiment, the method may include any preceding embodiment wherein the fitted parameters are determined so as to minimise differences between concentrations of the surfactant species in the non-micellar pseudo-phase as calculated by the thermodynamic model and those concentrations according to the distributions resulting from the simulations.

Embodiments may include a method comprising the method of any preceding embodiment, and further comprising making the mixture of two or more surfactant species so as to have one or more of the estimated properties. In an alternative embodiment, the method may include wherein the made mixture has a ratio of the two or more surfactant species which is estimated using the thermodynamic model and fitted parameters to have a predefined target critical micelle concentration. In an alternative embodiment, the method may include an preceding embodiment wherein the mixture is comprised within one of: a cosmetic product, a food or drink product, a cleaning product, a lubricant, a medicament, and a paint. In an alternative embodiment, the method may include one or more computer readable media comprising computer program code arranged to carry out the steps of any of preceding embodiments when executed on one or more suitable computer systems.

The embodiments may include an apparatus for modelling a mixture of two or more surfactant species, comprising: a molecular dynamics simulator arranged to perform a plurality of molecular dynamics simulations of the mixture, each simulation using a particular total concentration of the surfactant species and a particular ratio of the surfactant species, such that the plurality of simulations cover a plurality of such total concentrations and a plurality of such ratios, each simulation being carried out above the critical micelle concentration of the simulated mixture; a distribution analyser arranged to determine, for each simulation, and from the results of each simulation, a distribution of each surfactant species between at least a micellar pseudo-phase and a non-micellar pseudo-phase of the mixture at the particular total concentration and particular ratio for that simulation; and a parameter fitting unit arranged to fit a thermodynamic model of the mixture to the distributions to determine fitted parameters of the thermodynamic model. In an alternative embodiment, the apparatus may include a property estimator unit arranged to estimate one or more properties of the mixture of the two or more surfactant species using the thermodynamic model and the fitted parameters. In an alternative embodiment, the apparatus may include wherein the one or more properties comprise one or more of: the critical micelle concentration of the mixture at one or more ratios of the surfactant species; a ratio of the two or more surfactant species estimated to provide the mixture with a target critical micelle concentration; and one or more properties of a mixture of surfactants comprising the two or more surfactant species, and one or more further surfactant species. In an alternative embodiment, the apparatus may include any preceding embodiment wherein the thermodynamic model comprises a pseudo-phase separation model (PSM). In an alternative embodiment, the apparatus may include any preceding embodiment wherein the fitted parameters comprise a plurality of non-ideal mixing parameters representing mixing of the two or more surfactant species in the micellar pseudo-phase, the non-ideal mixing parameters being used in the thermodynamic model to determine an activity coefficient for each surfactant species within the micellar pseudo-phase. In an alternative embodiment, the apparatus may include wherein the non-ideal mixing parameters are constants, for the mixture of surfactant species, of a Margules model or other mixing model incorporated within the thermodynamic model. In an alternative embodiment, the apparatus may include any preceding embodiment wherein the parameter fitting unit is arranged to determine the parameters by fitting so as to minimise differences between concentrations of the surfactant species in the non-micellar pseudo-phase as calculated using the thermodynamic model and those concentrations according to the distributions resulting from the simulations.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the disclosed embodiments or of what may be claimed, but rather as descriptions of features specific to particular embodiments of the disclosed embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

It is therefore intended that the foregoing detailed description be regarded as illustrative rather than limiting, and that it be understood that it is the following claims, including all equivalents, that are intended to define the spirit and scope of this invention.

What is claimed is:

1. A computer implemented method of automatically generating a model of a mixture of two or more surfactant species from which one or more properties thereof may be estimated to facilitate manufacture of the mixture having the one or more properties, comprising:
    performing, automatically by a processor, a plurality of molecular dynamics simulations of the mixture, each simulation using a particular total concentration of the surfactant species and a particular ratio of the surfactant species, such that the plurality of simulations cover a plurality of such total concentrations and a plurality of such ratios, each simulation being carried out above a critical micelle concentration of the simulated mixture;
    determining, by the processor for each simulation, and from results of each simulation, a distribution of each surfactant species between at least a micellar pseudo-phase and a non-micellar pseudo-phase of the mixture at the particular total concentration and particular ratio for that simulation;
    generating, by the processor, the model by fitting a thermodynamic model of the mixture to the distributions to determine fitted parameters of the thermodynamic model; and
    estimating, by the processor, the one or more properties using the fitted thermodynamic model and the fitted parameters; and
    wherein the estimated one or more properties are used to facilitate manufacture of the mixture having the estimated one or more properties.

2. The method of claim 1 wherein the one or more properties comprise the critical micelle concentration of the mixture at one or more ratios of the surfactant species.

3. The method of claim 1 wherein the one or more properties comprise a ratio of the two or more surfactant species estimated to provide the mixture with a target critical micelle concentration.

4. The method of claim 1, wherein the one or more properties comprise one or more properties of a mixture of surfactants comprising the two or more surfactant species, and one or more further surfactant species.

5. The method of claim 1 wherein the thermodynamic model comprises a pseudo-phase separation model (PSM).

6. The method of claim 1 wherein the fitted parameters comprise a plurality of non-ideal mixing parameters representing mixing of the two or more surfactant species in the micellar pseudo-phase, the non-ideal mixing parameters being used in the thermodynamic model to determine an activity coefficient for each surfactant species within the micellar pseudo-phase.

7. The method of claim 6 wherein the non-ideal mixing parameters are constants, for the mixture of surfactant species, of a Margules model or other non-ideal mixing model incorporated within the thermodynamic model.

8. The method of claim 1 wherein the fitted parameters are determined so as to minimise differences between concentrations of the surfactant species in the non-micellar pseudo-phase as calculated by the thermodynamic model and those concentrations according to the distributions resulting from the simulations.

9. The method of claim 1, further comprising making the mixture of two or more surfactant species so as to have one or more of the estimated properties.

10. The method of claim 9 wherein the made mixture has a ratio of the two or more surfactant species which is estimated using the thermodynamic model and fitted parameters to have a predefined target critical micelle concentration.

11. The method of claim 9 wherein the mixture is comprised within one of: a cosmetic product, a food or drink product, a cleaning product, a lubricant, a medicament, and a paint.

12. One or more non-transitory computer readable media comprising computer program code arranged to carry out the following steps when executed on one or more suitable computer systems:
    performing a plurality of molecular dynamics simulations of a mixture of two or more surfactant species, each simulation using a particular total concentration of the surfactant species and a particular ratio of the surfactant species, such that the plurality of simulations cover a plurality of such total concentrations and a plurality of such ratios, each simulation being carried out above a critical micelle concentration of the simulated mixture;
    determining, for each simulation, and from results of each simulation, a distribution of each surfactant species of the mixture between at least a micellar pseudo-phase and a non-micellar pseudo-phase of the mixture at the particular total concentration and particular ratio for that simulation;
    fitting a thermodynamic model of the mixture to the distributions to determine fitted parameters of the thermodynamic model;
    estimating one or more properties of the mixture using the thermodynamic model and the fitted parameters; and
    facilitating manufacture of the mixture having the estimated one or more properties.

13. The one or more non-transitory computer readable media of claim 12 wherein the one or more properties comprise the critical micelle concentration of the mixture at one or more ratios of the surfactant species.

14. An apparatus for modelling a mixture of two or more surfactant species, comprising:
    a processor and a non-transitory memory coupled therewith, the non-transitory memory having stored therein computer executable instruations which, when executed by the processor, cause the processor to implement:
    a molecular dynamics simulator arranged to perform a plurality of molecular dynamics simulations of the mixture, each simulation using a particular total concentration of the surfactant species and a particular ratio of the surfactant species, such that the plurality of simulations cover a plurality of such total concentrations and a plurality of such ratios, each simulation being carried out above a critical micelle concentration of the simulated mixture;
    a distribution analyser arranged to determine, for each simulation, and from results of each simulation, a distribution of each surfactant species between at least a micellar pseudo-phase and a non-micellar pseudo-phase of the mixture at the particular total concentration and particular ratio for that simulation; and
    a parameter fitting unit arranged to fit a thermodynamic model of the mixture to the distributions to determine fitted parameters of the thermodynamic model; and
    wherein manufacture of the mixture having the estimated one or more properties is facilitated hereby.

15. The apparatus of claim 14 further comprising a property estimator unit arranged to estimate one or more properties of the mixture of the two or more surfactant species using the thermodynamic model and the fitted parameters.

16. The apparatus of claim 15 wherein the one or more properties comprise one or more of: the critical micelle concentration of the mixture at one or more ratios of the surfactant species; a ratio of the two or more surfactant species estimated to provide the mixture with a target critical micelle concentration; and one or more properties of a mixture of surfactants comprising the two or more surfactant species, and one or more further surfactant species.

17. The apparatus of claim 14 wherein the thermodynamic model comprises a pseudo-phase separation model (PSM).

18. The apparatus of claim 14 wherein the fitted parameters comprise a plurality of non-ideal mixing parameters representing mixing of the two or more surfactant species in the micellar pseudo-phase, the non-ideal mixing parameters being used in the thermodynamic model to determine an activity coefficient for each surfactant species within the micellar pseudo-phase.

19. The apparatus of claim 18 wherein the non-ideal mixing parameters are constants, for the mixture of surfactant species, of a Margules model or other mixing model incorporated within the thermodynamic model.

20. The apparatus of claim 14 wherein the parameter fitting unit is arranged to determine the parameters by fitting so as to minimise differences between concentrations of the surfactant species in the non-micellar pseudo-phase as calculated using the thermodynamic model and those concentrations according to the distributions resulting from the simulations.

* * * * *